United States Patent
Soler et al.

(10) Patent No.: US 9,844,116 B2
(45) Date of Patent: Dec. 12, 2017

(54) SYSTEMS AND METHODS FOR CONTROLLING THE SPECTRAL CONTENT OF LED LIGHTING DEVICES

(71) Applicant: Biological Innovation & Optimization Systems, LLC, Melbourne, FL (US)

(72) Inventors: Robert Soler, San Marcos, CA (US); Eric Thosteson, Satellite Beach, FL (US); Eliza Balestracci, Satellite Beach, FL (US)

(73) Assignee: Biological Innovation & Optimization Systems, LLC, Melbourne, FL (US)

( * ) Notice: Subject to any disclaimer, the term of this patent is extended or adjusted under 35 U.S.C. 154(b) by 0 days.

(21) Appl. No.: 15/364,533

(22) Filed: Nov. 30, 2016

(65) Prior Publication Data
US 2017/0086274 A1    Mar. 23, 2017

Related U.S. Application Data

(63) Continuation-in-part of application No. 15/264,197, filed on Sep. 13, 2016.

(60) Provisional application No. 62/218,946, filed on Sep. 15, 2015, provisional application No. 62/323,021, filed on Apr. 15, 2016, provisional application No. 62/380,842, filed on Aug. 29, 2016.

(51) Int. Cl.
| | |
|---|---|
| *H05B 33/08* | (2006.01) |
| *H05B 37/02* | (2006.01) |
| *A61M 21/00* | (2006.01) |
| *A61N 5/06* | (2006.01) |

(52) U.S. Cl.
CPC ......... *H05B 33/0866* (2013.01); *A61M 21/00* (2013.01); *A61N 5/0618* (2013.01); *H05B 33/0815* (2013.01); *H05B 33/0851* (2013.01); *H05B 37/0227* (2013.01); *A61M 2021/0044* (2013.01); *A61N 2005/0651* (2013.01); *A61N 2005/0663* (2013.01)

(58) Field of Classification Search
CPC ............ H05B 33/0833; H05B 33/0848; H05B 33/0851; H05B 33/0854; H05B 33/0857; H05B 33/086; H05B 33/0866; A61M 21/00; A61M 21/0005; A61M 21/0044; A61N 5/06; A61N 5/0613; A61N 5/0618
See application file for complete search history.

(56) References Cited

U.S. PATENT DOCUMENTS

| | | |
|---|---|---|
| 3,869,605 A | 3/1975 | Davis |
| 3,931,695 A | 1/1976 | Widmayer |
| 4,768,390 A | 9/1988 | Baker et al. |
| 5,012,609 A | 5/1991 | Ignatius et al. |
| 5,253,302 A | 10/1993 | Massen |
| 5,299,383 A | 4/1994 | Takakura et al. |

(Continued)

*Primary Examiner* — Jason M Crawford
(74) *Attorney, Agent, or Firm* — OIPWC, LLC

(57) ABSTRACT

Systems and methods for improving color accuracy and uniformity in LED illumination systems are disclosed including light engines, switching circuits and methods of adding phosphors or lumiphoric materials for controlling the addition or subtraction of light from one or more color light sources of the light engines to produce light of a uniform and consistent color. Systems and methods of providing LED light engines and associated illumination spectrums that are both visually appealing, rich in melanopic flux and that reduce blue light hazard exposure are also disclosed.

20 Claims, 11 Drawing Sheets

(56) References Cited

U.S. PATENT DOCUMENTS

| | | |
|---|---|---|
| 5,606,821 A | 3/1997 | Sadjadi et al. |
| 5,813,753 A | 9/1998 | Vriens et al. |
| 5,851,063 A | 12/1998 | Doughty et al. |
| 5,959,316 A | 9/1999 | Lowery |
| 6,294,800 B1 | 9/2001 | Duggal et al. |
| 6,357,889 B1 | 3/2002 | Duggal et al. |
| 6,441,558 B1 | 8/2002 | Muthu et al. |
| 6,459,919 B1 | 10/2002 | Lys et al. |
| 6,538,371 B1 | 3/2003 | Duggal et al. |
| 6,552,495 B1 | 4/2003 | Chang |
| 6,554,439 B1 | 4/2003 | Teicher et al. |
| 6,554,450 B2 | 4/2003 | Fang et al. |
| 6,577,080 B2 | 6/2003 | Lys et al. |
| 6,586,882 B1 | 7/2003 | Harbers |
| 6,636,003 B2 | 10/2003 | Rahm et al. |
| 6,641,283 B1 | 11/2003 | Bohler |
| 6,680,200 B2 | 1/2004 | Everett |
| 6,685,852 B2 | 2/2004 | Setlur et al. |
| 6,734,465 B1 | 5/2004 | Taskar et al. |
| 6,880,291 B2 | 4/2005 | Raun et al. |
| 6,914,265 B2 | 7/2005 | Bawendi et al. |
| 6,921,182 B2 | 7/2005 | Anderson, Jr. et al. |
| 6,936,857 B2 | 8/2005 | Doxsee et al. |
| 6,967,116 B2 | 11/2005 | Negley |
| 7,005,679 B2 | 2/2006 | Tarsa et al. |
| 7,008,559 B2 * | 3/2006 | Chen .................. C09K 11/574 252/301.4 R |
| 7,015,636 B2 | 3/2006 | Bolta |
| 7,034,934 B2 | 4/2006 | Manning |
| 7,058,197 B1 | 6/2006 | McGuire et al. |
| 7,125,143 B2 | 10/2006 | Hacker |
| 7,135,664 B2 | 11/2006 | Vornsand et al. |
| 7,215,074 B2 | 5/2007 | Shimizu et al. |
| 7,222,220 B2 | 5/2007 | Cypher et al. |
| 7,234,844 B2 | 6/2007 | Bolta et al. |
| 7,250,715 B2 | 7/2007 | Mueller et al. |
| 7,255,457 B2 | 8/2007 | Ducharme et al. |
| 7,256,557 B2 * | 8/2007 | Lim .................. G02F 1/133603 315/312 |
| 7,264,527 B2 | 9/2007 | Bawendi et al. |
| 7,319,293 B2 | 1/2008 | Maxik |
| 7,324,076 B2 | 1/2008 | Lee et al. |
| 7,365,485 B2 | 4/2008 | Fukasawa et al. |
| 7,382,091 B2 | 6/2008 | Chen et al. |
| 7,387,405 B2 | 6/2008 | Ducharme et al. |
| 7,520,607 B2 | 4/2009 | Casper et al. |
| 7,573,210 B2 | 8/2009 | Ashdown et al. |
| 7,598,686 B2 | 10/2009 | Lys et al. |
| 7,598,961 B2 | 10/2009 | Higgins |
| 7,678,140 B2 | 3/2010 | Brainard et al. |
| 7,679,281 B2 | 3/2010 | Kim et al. |
| 7,684,007 B2 | 3/2010 | Hull et al. |
| 7,703,943 B2 | 4/2010 | Li et al. |
| 7,728,846 B2 | 6/2010 | Higgins et al. |
| 7,748,845 B2 | 7/2010 | Casper et al. |
| 7,828,453 B2 | 11/2010 | Tran et al. |
| 7,845,823 B2 | 12/2010 | Mueller et al. |
| 7,972,030 B2 | 7/2011 | Li |
| 7,984,989 B2 | 7/2011 | Gruber |
| 8,038,314 B2 | 10/2011 | Ladewig |
| 8,115,419 B2 | 2/2012 | Given et al. |
| 8,192,047 B2 | 6/2012 | Bailey et al. |
| 8,207,676 B2 | 6/2012 | Hilgers |
| 8,253,336 B2 | 8/2012 | Maxik et al. |
| 8,256,921 B2 | 9/2012 | Crookham et al. |
| 8,297,783 B2 | 10/2012 | Kim |
| 8,324,808 B2 * | 12/2012 | Maxik .................. A61N 5/0618 315/32 |
| 8,324,823 B2 | 12/2012 | Choi et al. |
| 8,362,684 B2 | 1/2013 | Bawendi et al. |
| 8,378,574 B2 | 2/2013 | Schlangen et al. |
| 8,401,231 B2 | 3/2013 | Maxik et al. |
| 8,410,725 B2 | 4/2013 | Jacobs et al. |
| 8,441,210 B2 | 5/2013 | Shteynberg et al. |
| 8,446,095 B2 | 5/2013 | Maxik et al. |
| 8,513,875 B2 | 8/2013 | Van De Ven et al. |
| 8,547,391 B2 | 10/2013 | Maxik et al. |
| 8,643,276 B2 | 2/2014 | Maxik et al. |
| 8,680,457 B2 | 3/2014 | Maxik et al. |
| 8,686,641 B2 | 4/2014 | Maxik et al. |
| 8,743,023 B2 | 6/2014 | Maxik et al. |
| 8,754,832 B2 | 6/2014 | Maxik et al. |
| 8,901,850 B2 | 12/2014 | Maxik et al. |
| 8,941,329 B2 | 1/2015 | Maxik et al. |
| 9,024,536 B2 | 5/2015 | Maxik et al. |
| 9,030,103 B2 | 5/2015 | Pickard |
| 9,036,244 B2 | 5/2015 | Maxik et al. |
| 9,039,746 B2 | 5/2015 | van de Ven et al. |
| 9,052,067 B2 | 6/2015 | van de Ven et al. |
| 9,127,818 B2 | 9/2015 | Maxik et al. |
| 9,131,573 B2 | 9/2015 | Maxik et al. |
| 9,137,874 B2 | 9/2015 | Maxik et al. |
| 9,173,269 B2 | 10/2015 | Maxik et al. |
| 9,174,067 B2 | 11/2015 | Maxik et al. |
| 9,220,202 B2 | 12/2015 | Maxik et al. |
| 9,265,968 B2 | 2/2016 | Maxik et al. |
| 9,289,574 B2 | 3/2016 | Maxik et al. |
| 9,322,516 B2 | 4/2016 | Boomgaarden et al. |
| 9,326,454 B2 | 5/2016 | Suzuki |
| 9,353,916 B2 | 5/2016 | Maxik et al. |
| 9,441,793 B2 | 9/2016 | Van De Ven et al. |
| 2001/0002049 A1 | 5/2001 | Reeh et al. |
| 2001/0047618 A1 | 12/2001 | Fang et al. |
| 2002/0026659 A1 | 2/2002 | Blowers et al. |
| 2003/0005626 A1 | 1/2003 | Yoneda et al. |
| 2003/0009933 A1 | 1/2003 | Yoneda et al. |
| 2004/0052076 A1 | 3/2004 | Mueller |
| 2004/0105261 A1 | 6/2004 | Ducharme et al. |
| 2004/0109302 A1 | 6/2004 | Yoneda et al. |
| 2004/0217364 A1 | 11/2004 | Tarsa et al. |
| 2004/0218387 A1 * | 11/2004 | Gerlach .................. F21K 9/00 362/231 |
| 2004/0259363 A1 | 12/2004 | Bawendi et al. |
| 2004/0264193 A1 | 12/2004 | Okumura |
| 2005/0030744 A1 | 2/2005 | Ducharme et al. |
| 2005/0267213 A1 | 12/2005 | Gold et al. |
| 2005/0281027 A1 | 12/2005 | Capen et al. |
| 2006/0002110 A1 | 1/2006 | Dowling et al. |
| 2006/0053691 A1 | 3/2006 | Harwood et al. |
| 2006/0104058 A1 | 5/2006 | Chemel et al. |
| 2006/0105482 A1 | 5/2006 | Alferink et al. |
| 2006/0138435 A1 | 6/2006 | Tarsa et al. |
| 2006/0152140 A1 | 7/2006 | Brandes |
| 2006/0152172 A9 | 7/2006 | Mueller et al. |
| 2006/0164005 A1 | 7/2006 | Sun |
| 2006/0181192 A1 | 8/2006 | Radkov et al. |
| 2007/0058368 A1 | 3/2007 | Partee et al. |
| 2007/0170447 A1 | 7/2007 | Negley et al. |
| 2007/0276606 A1 | 11/2007 | Radkov et al. |
| 2007/0289207 A1 | 12/2007 | May et al. |
| 2008/0119912 A1 | 5/2008 | Hayes |
| 2008/0302004 A1 | 12/2008 | Lin |
| 2009/0199470 A1 | 8/2009 | Capen et al. |
| 2009/0288340 A1 | 11/2009 | Hess |
| 2010/0020536 A1 * | 1/2010 | Bafetti .................. F21V 23/003 362/231 |
| 2010/0076620 A1 | 3/2010 | Loebl et al. |
| 2010/0121420 A1 | 5/2010 | Fiset et al. |
| 2010/0207544 A1 * | 8/2010 | Man .................. H05B 33/0857 315/294 |
| 2010/0244735 A1 | 9/2010 | Buelow, II |
| 2010/0244740 A1 | 9/2010 | Alpert et al. |
| 2010/0287830 A1 | 11/2010 | Chen et al. |
| 2011/0115385 A1 | 5/2011 | Waumans et al. |
| 2011/0133654 A1 * | 6/2011 | McKenzie .................. F21K 9/00 315/152 |
| 2011/0162101 A1 | 6/2011 | Cahoon et al. |
| 2011/0205738 A1 | 8/2011 | Peifer et al. |
| 2011/0209400 A1 | 9/2011 | Rooymans |
| 2011/0242453 A1 | 10/2011 | Van De Ven et al. |
| 2012/0003728 A1 | 1/2012 | Lanoue et al. |
| 2012/0218750 A1 | 8/2012 | Klase et al. |
| 2012/0286699 A1 * | 11/2012 | Yan .................. H05B 33/0866 315/294 |

(56) References Cited

U.S. PATENT DOCUMENTS

| | | |
|---|---|---|
| 2013/0021792 A1 | 1/2013 | Snell et al. |
| 2013/0114242 A1* | 5/2013 | Pickard .................... F21V 9/16 362/84 |
| 2013/0255150 A1 | 10/2013 | Karpinski et al. |
| 2013/0278148 A1 | 10/2013 | Maxik et al. |
| 2013/0278172 A1 | 10/2013 | Maxik et al. |
| 2013/0293148 A1 | 11/2013 | Maxik et al. |
| 2014/0015438 A1 | 1/2014 | Maxik et al. |
| 2014/0049191 A1 | 2/2014 | Maxik et al. |
| 2014/0049192 A1 | 2/2014 | Maxik et al. |
| 2014/0185281 A1 | 7/2014 | Lee et al. |
| 2014/0215911 A1 | 8/2014 | Suzuki |
| 2014/0228914 A1* | 8/2014 | van de Ven .......... A61N 5/0618 607/88 |
| 2014/0232288 A1* | 8/2014 | Brandes ............. H05B 33/0803 315/250 |
| 2014/0259905 A1 | 9/2014 | Ovadya et al. |
| 2014/0330406 A1 | 11/2014 | Faris |
| 2014/0375222 A1* | 12/2014 | Rains, Jr. ........... H05B 37/0245 315/158 |
| 2015/0128489 A1 | 5/2015 | Yamada et al. |
| 2015/0223402 A1 | 8/2015 | Krijn et al. |
| 2016/0037730 A1 | 2/2016 | Whittingham |

* cited by examiner

SYSTEMS AND METHODS FOR CONTROLLING THE SPECTRAL CONTENT OF LED LIGHTING DEVICES

RELATED APPLICATIONS

This application is a continuation-in-part application of U.S. patent application Ser. No. 15/264,197, entitled SYSTEMS AND METHODS FOR CONTROLLING THE SPECTRAL CONTENT OF LED LIGHTING DEVICES, filed Sep. 13, 2016. This application also claims priority to and the benefit of U.S. Provisional Application No. 62/323,021, filed Apr. 15, 2016, and U.S. Provisional Application No. 62/380,842, filed Aug. 29, 2016. The contents of each of the aforementioned patent applications are incorporated herein in their entireties.

Except to the extent that any of the disclosure in the referenced patents conflicts with the disclosure herein, the following US patents, which include inter alia disclosure pertaining to light emitting diodes, LED luminaires and light engines, color mixing, power delivery, LED driving and switching methods and systems, and phosphors and other lumiphoric materials and their application in LED technologies are incorporated herein by reference in their entireties: U.S. Pat. Nos. 7,744,243, 7,317,403, 7,358,954 and 8,749,160, 9,309,461, 9,231,172, 8,900,892, 8,736,036, 8,597,963, 8,329,485 and 6,635,987.

FIELD OF THE INVENTION

Embodiments of the invention relate generally to systems and methods for improving color accuracy and uniformity in LED illumination systems and for providing lighting with high melanopic flux and consistent color points.

BACKGROUND OF THE INVENTION

Light emitting diode (LED) technology is a maturing technology that continues to show improvements in efficiency, customability and cost reduction. LED technology is rapidly being deployed in a host of industries and markets including general lighting for homes, offices, and transportation, solid state display lighting such as in LCDs, aviation, agricultural, medical, and other fields of application. The increased energy efficiency of LED technology compared with other lighting solutions coupled with the reduction of costs of LED themselves are increasing the number of LED applications and rate of adoptions across industries. While LED technology promises greater reliability, longer lifetimes and greater efficiencies than other lighting technologies, the ability to mix and independently drive different color LEDs to produce customized and dynamic light output makes LED technology and solid state lighting (SSL) in general robust platforms to meet the demands of a variety of market needs and opens the door to many new applications of these lighting technologies. The ability to tailor and tune the output spectra of LED fixtures and dynamically switch individual LEDs "on-the-fly", for example in response to an environmental cue, dramatically opens up the application space of solid state lighting.

As is well known in the art, LED luminaires generally comprise one or more individual LEDs dies or packages mounted on a circuit board. The LEDs may be electrically connected together on a single channel or be distributed and electrically driven across multiple independent channels. The LEDs are typically powered by current from an associated LED driver or power supply. Examples of these power supply drivers include AC/DC and DC/DC switched mode power supplies (SMPS). Examples of LED power drivers include power supplies designed to supply constant current to the LED string in order to maintain a consistent and steady light output from the LEDs. LEDs may also be powered by an AC power source. Direct AC power typically undergoes rectification and other power conditioning prior to being deliver to the LEDs. LED luminaires may also comprise an optic or diffuser, a heat sink and other structural components.

Although LEDs may be combined in such a way to deliver a wide variety of specific color outputs, LED luminaires for general lighting typically are designed to produce white light. Light perceived as white or near-white may be generated by a combination of red, green, and blue (RGB) LEDs. Output color of such a device may be altered by color mixing, for instance varying the amount of illumination produced by each of the respective color LEDs by adjusting the supply of current to each of the red, green, and blue LEDs. Another method for generating white or near-white light is by using a lumiphor such as a phosphor in conjunction with a blue "pump" LED. Still another approach for producing white light is to stimulate phosphors or dyes of multiple colors with an LED source. Many other approaches can also be taken.

Correlated Color Temperature (CCT), measured in degrees Kelvin (K), is a common a metric to characterize broad band light sources. CCT was introduced to address broadband light sources that may not be modeled by a blackbody radiator. CCT is defined as the temperature of a blackbody radiator whose chromaticity point is closest to the chromaticity point of the non-planckian light source. Every illumination source has a (radiometric) spectral power distribution whose output can be expressed as the integral of radiant power over the wavelength range of the light-emitting source. The eyes perception of this source can be expressed as a single chromaticity value, an ordered pair in a planar color-space (CCx, CCy), according to CIE1931 color space diagram. Other color spaces exist.

FIG. 1 is an example CIE 1931 diagram that illustrates, inter alia, the planar color-space with associated set of coordinates (x,y) representing perceived colors. The perceived color of any light source can be defined as a location on the color space. Individual LEDs are typically characterized by chromaticity (i.e., an x, y coordinate pair in the CIE color space) and luminous flux ($\phi=Y$) weighted by the luminous efficiency function ($V\lambda$). To create white light from multiple LED sources with varying wavelengths and intensities, LEDs may be mixed such that the resulting output matches a specific coordinate on the color-space plane.

FIG. 2 shows example spectral power distributions (SPDs) from conventional white light LEDs of three different correlated color temperatures. For each of these white light LED sources, the peak at around 450 nm represents the light contribution from a blue "pump" LED and the broader peak, for example and light above 500 nm, is due to the luminescence of one or more phosphors that have been excited by the blue light. In these conventional LED white light sources there is a trough of spectral power in the region around 490 nm.

LEDs, as with all manufactured products, have material and process variations that yield products with corresponding variation in performance. At present, LED manufacturers are challenged to produce uniform color points in their white LEDs and are limited to a "bandwidth spread" in their monochromatic LEDs as well. There are a number of reasons for this inability to achieve mass production of LEDs with uniform color points, key among them t are related to the packaging of the LEDs. There may be considerable variability from LED to LED, particularly in the case of phosphor converted LEDs, since both the variability of the LED chip and the phosphor coating can introduce variability into the performance of the final packaged LED. While the manufacturers of the packaged LEDs typically "bin" the final packaged LEDs to provide products of similar light and color output, even LEDs in the same bin will exhibit variations in color output.

Additionally, the light conversion efficiency of a specific LED and any associated phosphor coating may depend on the temperature at which the LED operates and how the LED is driven electrically. Differently packaged LEDs, even those within the same bin and that have the same light output at one temperature and drive current, may have different light output at other temperatures and/or drive currents. In many circumstances, until the packages are assembled into an operational luminaire or lighting device, the extent of any such variability cannot be fully determined.

Although embodiments of the invention are not dependent on such, it is believed that the gap in spectral power output between 480 and 500 nm, with a trough around 490 nm, that exists in conventional white light LEDs (e.g., as shown in FIG. 2) is a result of the LED industry recognizing the challenges posed in color uniformity when employing light in the aforementioned region. The retinal response over this region (e.g., 480-500 nm), is such that the eye and visual system is extremely discriminative of light and light color in this spectral region. For example; and as can be seen in FIG. 1, the CIE color space diagram, the variation in perceived color, as represented by the variation in color points over this 20 nm range between 480 nm and 500 nm is relatively large, for instance when compared with the perceived color changes in the region of 440 nm to 460 nm.

Additionally, LED manufacturers who make monochromatic LEDs, with a Full Width Half Maximum (FWHM) less than 40 nm, can typically only guarantee that any LED of a specific bin (i.e., within a certain color spectral bandwidth) will vary by no more than 5 nm in color output from another LED of the same bin. A lighting designer or manufacture attempting to construct a luminaire with a specific color output spectrum is challenged to provide a luminaire with consistent color output while using LEDs which may have an unacceptable wide range (e.g., 5 nm) of light output. Hence, because of the enhanced visual discrimination in the 480-500 nm color region, employing monochromatic LEDs in this region may result in unacceptable perceived color differences between LED fixtures that are designed to yield the some color output. Generating an LED spectrum with a consistent (x,y) color point while using monochromatic enhancement in the region from 480 nm-500 nm is a problematic challenge.

Melanopsin is a type of photopigment belonging to a larger family of light-sensitive retinal proteins called opsins, and is found in intrinsically photosensitive retinal ganglion cells (ipRGCs) of humans and other mammals. Melanopsin plays an important non-image-forming role in the photoentrainment of circadian rhythms as well as potentially many other physiologic functions. Stimulation of melanopsin-containing ipRGCs contributes to various reflexive responses of the brain and body to the presence of light. FIG. 3 shows the action spectrum of melanopsin 30 together with SPDs of conventional LED lights of different color temperatures 32. Melanopsin photoreceptors are sensitive to a range of wavelengths and reach peak light absorption at wavelengths around 480-500 (or 490) nanometers (nm). Recent scientific studies have shown that 480-500 nm light (the region of melanopic-producing light) light) is very important for non-visual stimuli including physiological and neurological effects such as pupillary light reflex and circadian entrainment. Conventional LED lighting fixtures provide less than optimal and potentially insufficient light in these biologically important wavelength ranges (e.g., non-visual stimulus) at standard light levels.

Blue Light Hazard", as defined by ANSI/IESNA RP-27.3-07, is the potential for a photochemically induced retinal injury resulting from radiation exposure primarily between 400 nm and 500 nm. Scientific data indicates that blue light can cause excessive amounts of reactive oxygen species in the retina, which may result in cumulative oxidative stress which can cause inter alia accelerated cellular aging in the retina. FIG. 3 illustrates the spectral region 34 associated with the blue light hazard. Even with conventional light levels, blue light exposure may cause long term damage over the course of years of exposure. This oxidative stress may be compounded and/or accelerated if the lighting illumination spectrum is deficient or depleted of light associated with non-visual stimulus. For example, the pupillary light reflex (PLR) is a reflex that controls the diameter of the pupil in response to the intensity (luminance) of light that falls on the retinal ganglion cells of the eye. This reflex thereby assists in, inter alia, adaptation to various levels of lightness or darkness. Insufficient stimulus of the RGCs, which may occur in the absence of sufficient melanopic light, that is light that falls within the melanopsin action spectrum region as shown in FIG. 3 and which provides the necessary stimulus of the RGCs, may result in reduced pupillary constriction, thereby allowing more blue light to enter the eye potentially resulting in increased and accelerated oxidative stress on the retina.

There is a need for general lighting device that delivers white light with excellent color rendering and esthetic characteristics and provides sufficient flux of melanopic light and generates sufficient spectral power in the relevant wavelengths to provide adequate non-visual stimulus associated with important physiological responses and functions. There is a need for lighting that reduces oxidative stress on the retina that results from blue light exposure.

In view of the enhanced human visual sensitivity in the 480-500 nm region and the inherent binning limitations of LEDs packages and the associated variability of color output of these LEDs, there is a need for methods for achieving and lighting devices that achieve consistent color temperature and color points while providing light of adequate or optimal melanopic flux.

Conventional white light producing LED technology commonly employs a monochromatic LED die or chip that produces a narrow band of blue or violet light that excites down-converting phosphors with broad emission spectrums to produce a resultant white light output. These monochromatic LEDS, with peak wavelengths typically in the spectral region between royal blue and near ultra violet region are commonly referred to as "pumps" since they, inter alia, provide relatively high energy light (e.g., blue) that excites or "pumps" a proximate phosphor (typically directly adjacent to the pump LED die). Conventional pump LEDs, i.e., those commonly used throughout the industry today, have a peak emissions between 420 nm and 450 nm. As discussed earlier herein, the blue light hazard region has a peak sensitivity plateau which spans the wavelengths between 420 nm and 450 nm. This spectral region corresponds almost precisely to range of the narrow band pump LED emission wavelengths. Thus, the range of optical frequencies used to excited broadband emission phosphors in conventional LED technology directly overlap the blue region known as blue light hazard.

Additionally, combinations of narrow band blue pump and broadband emission phosphor leads to a trough in the 490 nm region. This region has been shown to be at or near the peak sensitivity for the photopigment melanopsin. Melanopsin is located in retinal ganglion cells, which project directly to the suprachiasmatic nucleus and are believed to be heavily involved in circadian regulation. These retinal ganglion cells also are thought to drive brightness perception and pupil constriction.

As discussed above, light and in particular blue or bluish light may have both positive and negative effects on human circadian rhythms and regulation thereof depending on what type of light and how much light is received by the human visual system and the timing of such light exposure. Some lighting approaches use higher color temperatures as ways to maximize circadian impact. Examples of such color temperatures include 6500K, which correspond to daylight conditions. However, these 6500K spectrum LEDs are typically depleted of spectral energy in the 490 nm region and produce a large or heightened amount of 450 nm light. This conventional situation may pose health hazards including a potential retinal damage because the conventional white light producing LEDs, which do not have continuity between the melanopic region and the blue light hazard region, may result in inappropriate pupillary dilation during exposure to potentially harmful blue light blue light.

Recent scientific research has demonstrated the existence of an optical window in skin tissue, which that allows transmittance of red spectrums from 600-1000 nm. This optical window provides opportunity for absorption of red photons by chromaphore cytochrome c oxidase located in the mitochondria. This chromaphore leads to intercellular signaling and increased mitochondrial activity and potentially bistable support of daytime circadian signaling, which may synergistically work with retinal circadian photoreceptors.

BRIEF SUMMARY

Some embodiments include a method for generating illumination from a light source and tuning the spectral output of the light source comprising the steps of: providing a light engine comprising at least one LED of a first color, one LED of a second color, and one LED of a third color, electrically driving said light engine to produce a first illumination, providing a target color point illumination for the light engine, measuring the color of said first illumination and comparing it to said target color point, and adjusting the illumination output of one first color LED, one second color LED and one third color LED a by selectively electrically driving each of said first, second and third color LEDs such that the color of the resulting illumination output of the light engine matches said target color point illumination. In some embodiments, the LED of a first color is a white light producing LED, and the LED of the second color and the LED of the third color are each monochromatic LEDs. In some embodiments, the LED of the second color approximates the color cyan or about 490 nm and the LED of the third color approximates the color hyper-red or about 660 nm. In some embodiments, the measuring of the color output of said first illumination is performed using a measuring device separate from and not integrated with said light engine. In some embodiments, the adjusting the illumination output of the first color LED, the second color LED and the third color LED is accomplished by altering the electrical current operating conditions of each of the respective color LEDs, and is accomplished by programming an electrical switching circuit on the light engine such that an appropriate amount of current is provided to each of the color LEDs. In some embodiments, the target color illumination corresponds to a point on the C.I.E. chromaticity diagram on or proximal to the black body curve.

Other embodiments include methods and systems for controlling the output spectrum of a light engine comprising the steps of and systems elements for: measuring spectral characteristics of an illumination output of a light engine that is electrically driven to illumination wherein the light engine comprises a first color LED, a second color LED, a third color LED and a fourth color LED and converting said measured spectral characteristics to a measured chromaticity, comparing, said measured chromaticity with a target chromaticity, and selectively electrically driving the second color LED, the third color LED and the fourth color LED to produce respective illumination from one or more of said second, third, and fourth color LEDs such that the chromaticity of the illumination output of the light engine matches or approximates the target chromaticity. In some, embodiments the LED of the first color produces white light of a first color temperature, the LED of the second color produces white light of a second color temperature, and the LED of the third color and the LED of the fourth color are monochromatic LEDs. In some embodiments, the LED of the first color approximates a warm white color temperature of less than about 3000K and the LED of the second color approximates a neutral or cool white color temperature of greater than or equal to about 4000K. In some embodiments, the LED of the third color approximates the color cyan or about 490 nm, and the LED of the fourth color approximates the color hyper-red or about 660 nm. In other embodiments, the measuring of the spectral characteristics of the light engine illumination output is performed using a measuring device integrated with or into said light engine. In some embodiments, the adjusting the illumination output of the second color LED, the third color LED and the fourth color LED is accomplished by altering the amount of electrical current delivered to of each of the respective color LEDs. In some embodiments this is accomplished via a switching circuit comprising a microcontroller that is integral with said light engine.

Additional embodiments include a programmable LED light engine capable of being tuned to generate a specific spectral illumination output comprising a first color LED, a second color LED and a third color LED, means for electrically driving each of said color LED to produce an illumination output of the light engine, and means for adjusting the illumination output of each of the first color, second color and third color LEDs such that the illumination output of the light engine corresponds to an illumination output of a target color. Further embodiments include a programmable LED light engine that comprises means for measuring the spectral characteristics of the illumination output of the light engine, a processor that is programmed to compare a measured illumination output with a target color illumination output and to adjust the electrical operating point of (e.g., the amount of current flowing through) at least a portion of the LEDs such that the light engine illumination output color matches or approximates a target color output.

In some embodiments, primary spectrum control is defined through ratios and binning of polychromatic and monochromatic LEDs. In some embodiments, the preferred control circuitry is designed to provide fine control of the color point by using different color LEDs, each of which having biological significance above and beyond visual stimulus. In one embodiment, monochromatic LEDs are chosen such that blue LED color is greater or equal to about 465 nm, the green LED color is less than or equal to about 505 nm and red LED color is greater than or equal to about 626 nm. In some embodiments, the switching circuitry controls the distribution of current through the RGB color points such that the sum of all currents passing through the monochromatic LEDs (or other tuning LEDs), at any given time, equals the current passing through the entire light engine. In other embodiments, the control circuitry may also comprise a feedback circuit to adjust the output from each LED light source to correct any temperature-based color shifts as well as color shifts over the life of the light engine. The control circuit, in some embodiments, can use temperature feedback, such as a thermistor, or optical feedback, such as a photodiode or CCD, or any combination of the two.

In some embodiments, the method of tuning the light engine is performed at the point of light engine manufacture or distribution or point of sale. In other embodiments, the tuning of the light engine is performed iteratively and/or during routine operation of the light engine.

Embodiments of the present invention include a light engine comprising a switching circuit for controlling the addition or subtraction of light from one or more color light sources of the light engine to produce a light output that is consistent in color and is also rich in melanopic flux. Embodiments of the invention provide an illumination spectrum that is both visually appealing and uniform and with advantageous effects associated with a melanopic-rich flux. In some embodiments, a control circuit controls the current flow through one or more tuning LEDs to fine tune the chromaticity coordinates through a calibration process.

Some embodiments of the invention comprise a lighting device providing illumination that is not depleted in the melanopic region while maintaining consistent color temperature. Embodiments of the invention include light engines that provide illumination rich melanopic light as compared to conventional LED light sources. Some embodiments of the invention comprise a lighting device providing illumination that provides sufficient non-visual stimulus to protect or mitigate against blue light hazard and retinal oxidative stress. Some embodiments of the invention comprise a lighting device providing illumination that provides sufficient non-visual stimulus to facilitate the entrainment of the circadian rhythms of mammals.

DETAILED DESCRIPTION

Figure 1:
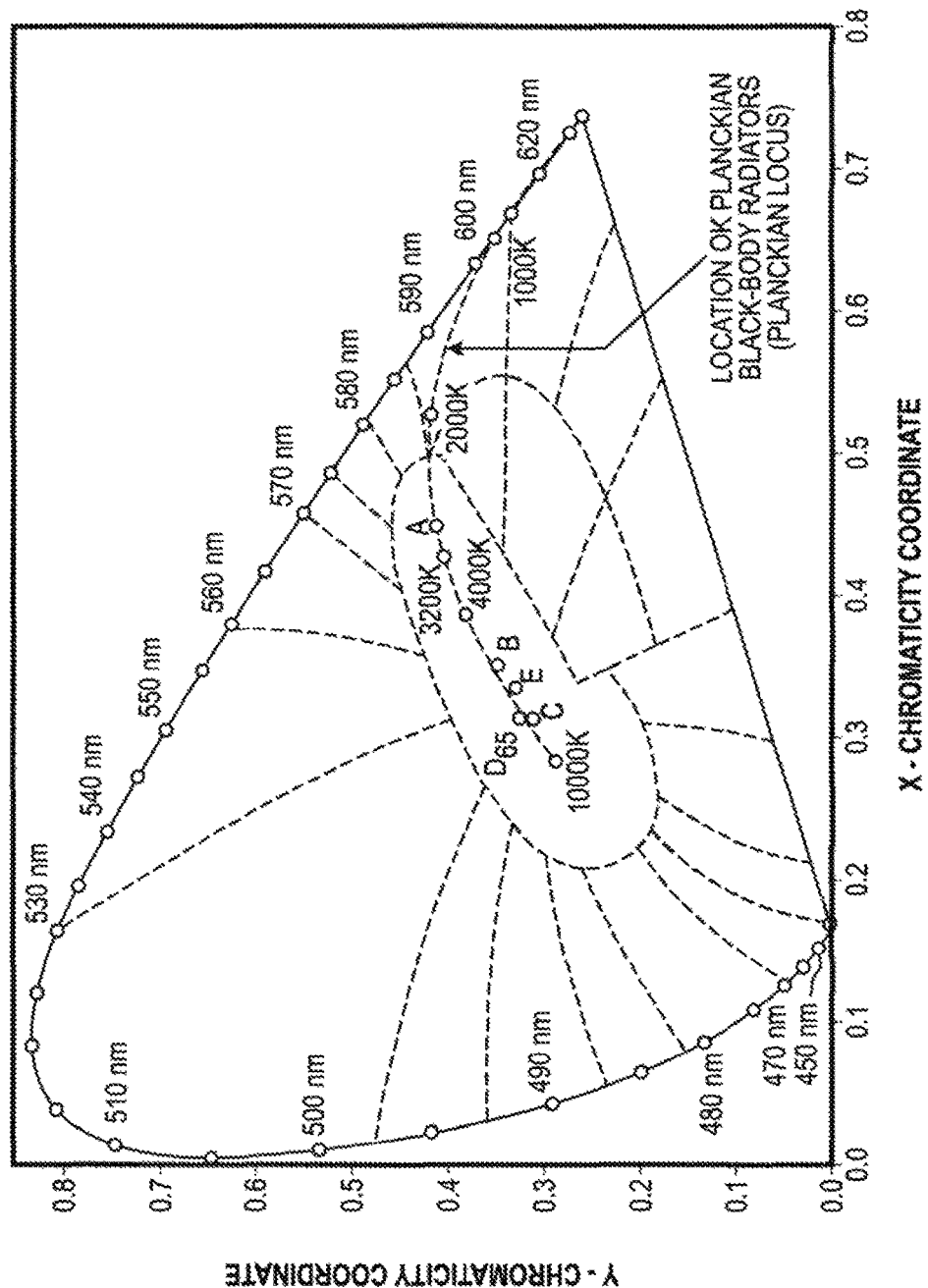
FIG. 1 is an example CIE diagram that shows the planar color-space with associated set of coordinates (x,y) representing perceived colors.
Figure 2:
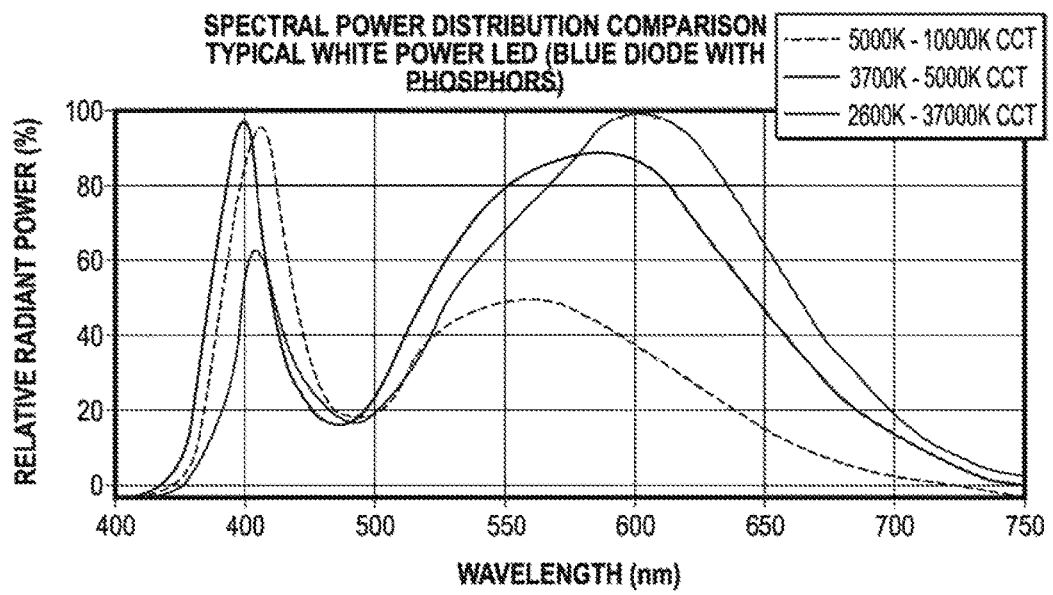
FIG. 2 shows example spectral power distributions (SPDs) from conventional white light LEDs of three different correlated color temperatures.
Figure 3:
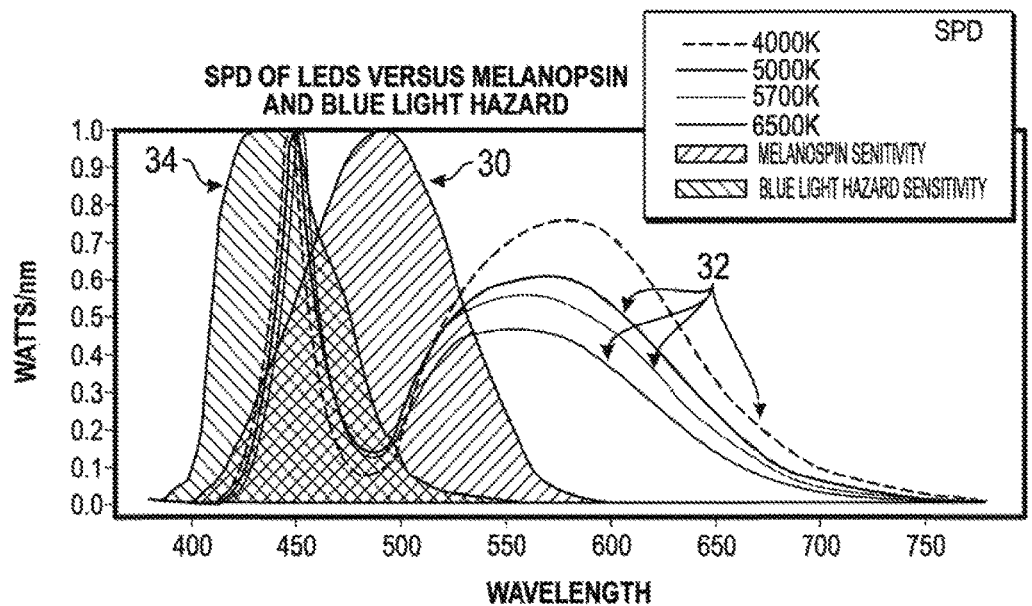
FIG. 3 shows the action spectrum of melanopsin and spectral region of blue light hazard overlaid and compared with the spectral power distributions (SPDs) from conventional white light LEDs of different CCTs.
Figure 4A:
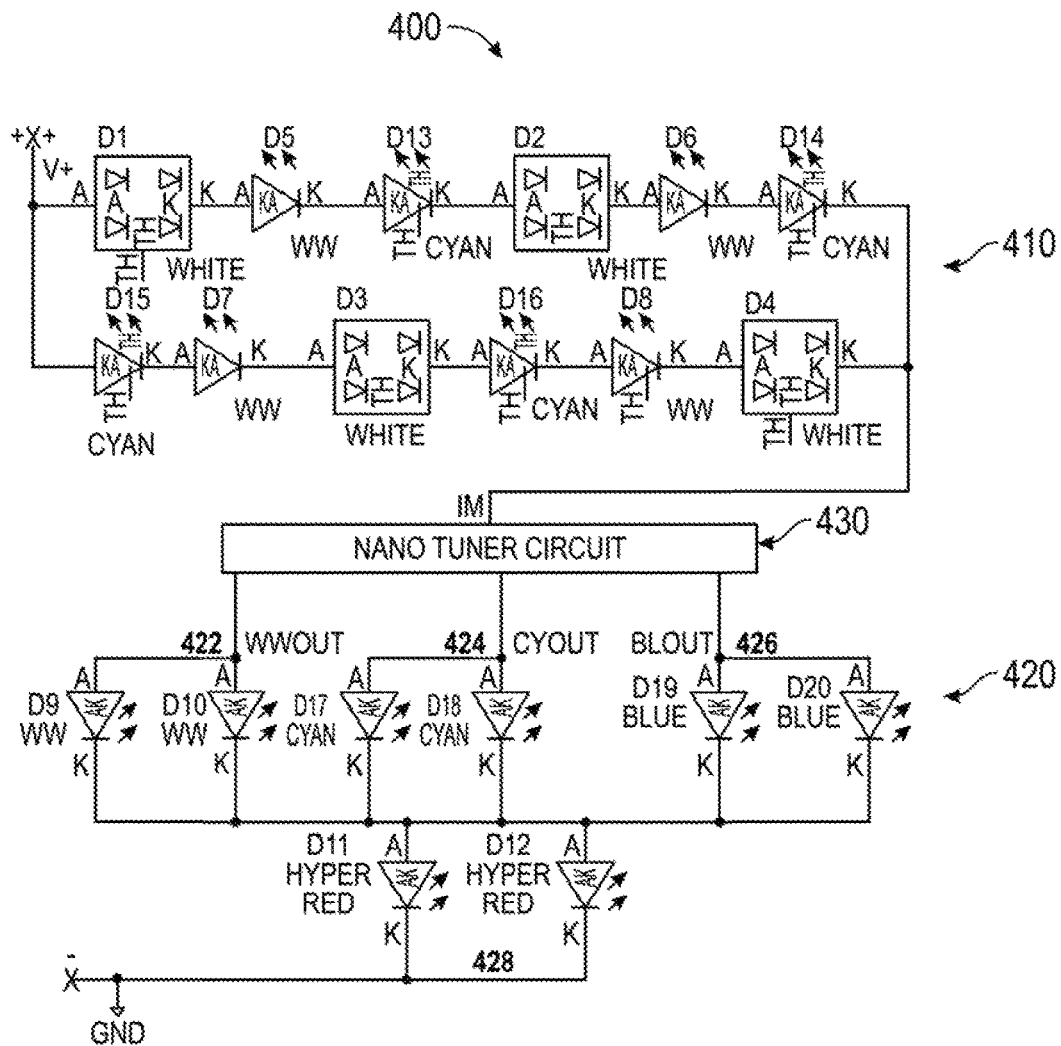
FIGS. 4a-b illustrate an LED light engine and associated switching circuitry according to some embodiments of the invention.
Figure 4B:
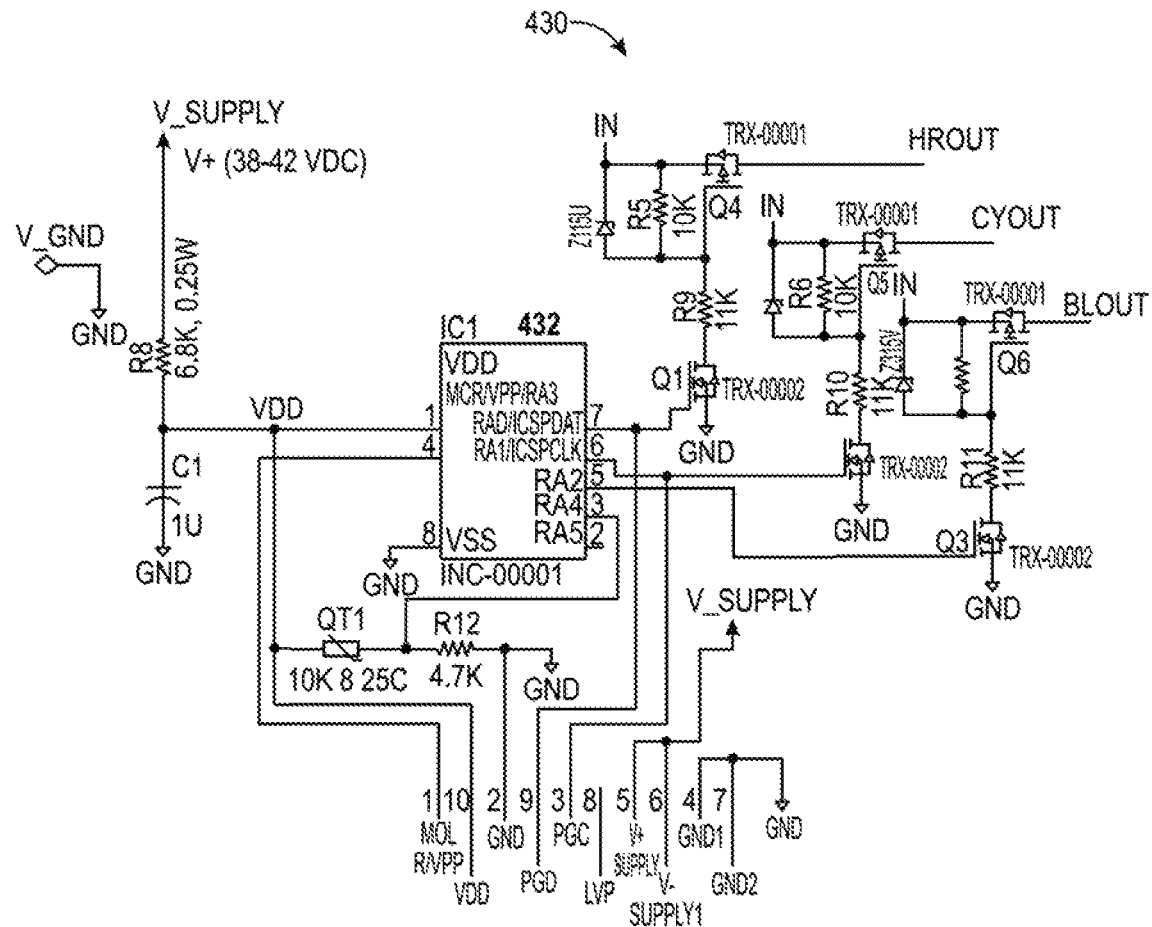

An embodiment of the invention comprises an LED light engine with integrated color tuning capability for providing uniform color output. FIGS. 4a-b illustrate an LED light engine and associated switching circuitry according to one embodiment. Referring to FIG. 4a, LED light engine 400 comprises: one or more strings of LED 410 that may be energized to produce a generally static output spectrum, for example a spectral output corresponding to white light; a set of tuning LEDs 420 for which the current through and corresponding light output may be modulated; and a nano-tuner circuit 430 for controlling the modulation of current and light output of the tuning LEDs. FIG. 4b illustrates the details of the nano-tuner switching circuitry represented by the nano-tuner block 430 in FIG. 4a according to one embodiment. Power to the LED board, and for powering the individual LEDs and integrated processors, may be provided by any conventional LED power supply or LED driver such as a class II power supply or other power delivery options as will be evident to those skilled in the an According to this embodiment, the LED light engine 400 contains a plurality of LEDs that are energized to produce an initial illumination output spectrum. In this example the following LEDs are used: Cree XHP35-4000K (White); Luxeon Z-Warm White (WW); ProLight PK2N-490 Cyan; Luxeon Z-480 nm Blue; and Luxeon Z-660 nm, Deep Red (Hyper Red). It is important to note that different LED packages may be used in embodiments of the invention, and the invention is not limited to specific LED packages. For example, alternative embodiments include the use of a single type white light LEDs, e.g., a cool white LED, and three monochromatic LEDs, e.g., blue, cyan and hyper-red.

Upon application of power, current flows through the LED string 410 and through the set of tuning LEDs 420. The nanotuner circuit 430 controls the current flow through each of the LEDs in the set of tuning LEDs 420. When power is supplied to the LED light engine 400, e.g., via a power supply or LED driver (not shown), current flows through both the LED string 410 and the set of tuning LEDs 420 to produce an output spectrum. In this example embodiment, the set of tuning LEDs 420 comprises a group of three different color LEDs, each of which is on its own separate channel and for which the current to and light output of may independently controlled by the nanotuner switching circuit 430. In this embodiment the three color channels are WW 422 (Luxeon Z—Warm White), Cyan 424 (ProLight-PK2N) and Blue 426 (Luxeon Z—Blue). The set of tuning LEDs 420 also includes a pair of hyper-red LEDs 428 (Luxeon Z Deep Red). The nanotuner circuit 430 (shown in detail in FIG. 4b) controls the current flow through each of the tuning LEDs 422, 424 and 426 by a selective switching that alters the current delivered to (and thereby the current that flows through) each of the tuning LED to achieve the desired output from each. The details of said switching are described further herein. HR LEDs 428 are continuously energized, and the total current through the HR LEDs 428 at any instant is equal to the total current through all the other tuning LEDs 422, 424 and 426 at that instant according to this embodiment, as will be evident from the circuit diagram of the LED light engine 400.

FIG. 4*b* illustrates the details of nano-tuner switching circuitry represented by the nano-tuner block 430 in FIG. 4*a*. The nanotuner circuit 430 includes a programmable microcontroller 432 which may be programmed to drive or switch the tuning LEDs in one or more specific ways. Examples of such switching algorithms are disclosed further herein. The microcontroller 432 used in this embodiment is Microchip PIC12F752/HV752, but embodiments of the invention are not limited to a specific microcontroller or specific circuit design and many variations are possible as will be evident to those skilled in the art. Effectively, the nanotuner circuit 430 acts, inter alia, as a switching circuit controlling the current that flows through each of the tuning LEDs (or strings of tuning LEDs). By opening and closing solid state "switches" to each of the tuning LEDs 422, 424 and 426, the microcontroller may alter the current delivered to each of the tuning LEDs thereby altering the intensity of light output from each type or color of the tuning LEDs. In this example, three different LED color types may be selectively and independently driven by altering the electrical current to each thereby producing a desired resultant output spectrum and color point. This provides for the fine tuning of spectral output across different LED boards that provides a means of insuring uniformity of output and chromaticity.

Operation of the system according to some embodiments will now be described. Powering up of the LED light engine 400 results in illumination of both the LED string 410 and the tuning LEDs 420 to produce an initial output spectrum. In one embodiment, at startup and initial powering, the current that flows through the each of the tuning LEDs 422, 424 and 426 is equally or near equally proportioned. For example, ⅓ of the total current flows through each of the three tuning LEDs 422, 424 and 426. However, no specific proportionality of current through the various tuning LED is required at startup and the ratio of currents may be adjusted as desired (e.g., using the nanotuner circuit 430 and programmable microcontroller).

Figure 5A:
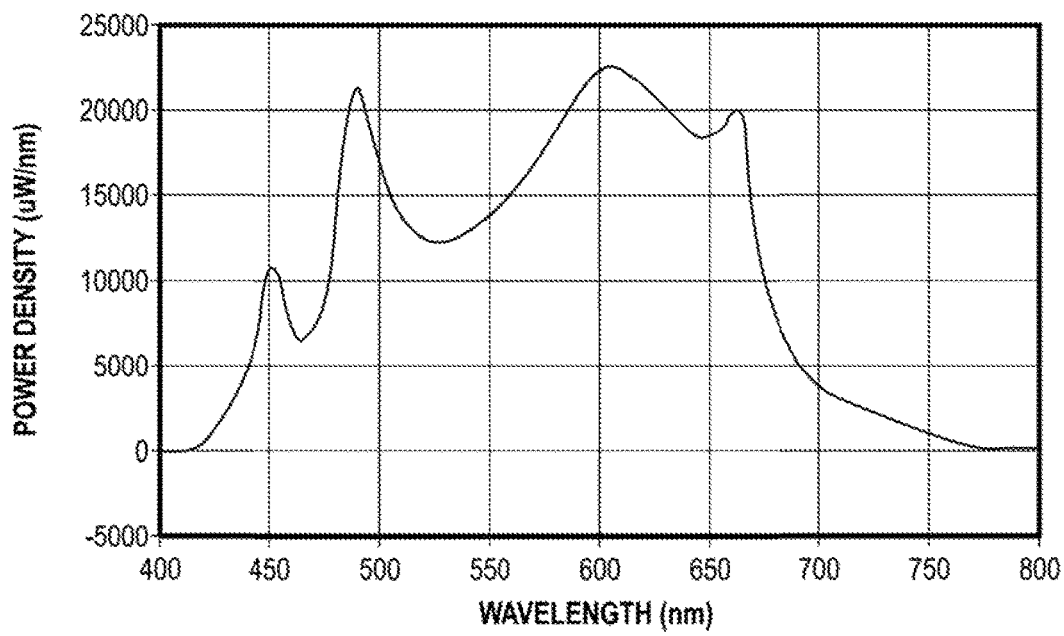
FIGS. 5a-b shows the spectral power distributions of LED light engines according to some embodiments of the invention.
Figure 5B:
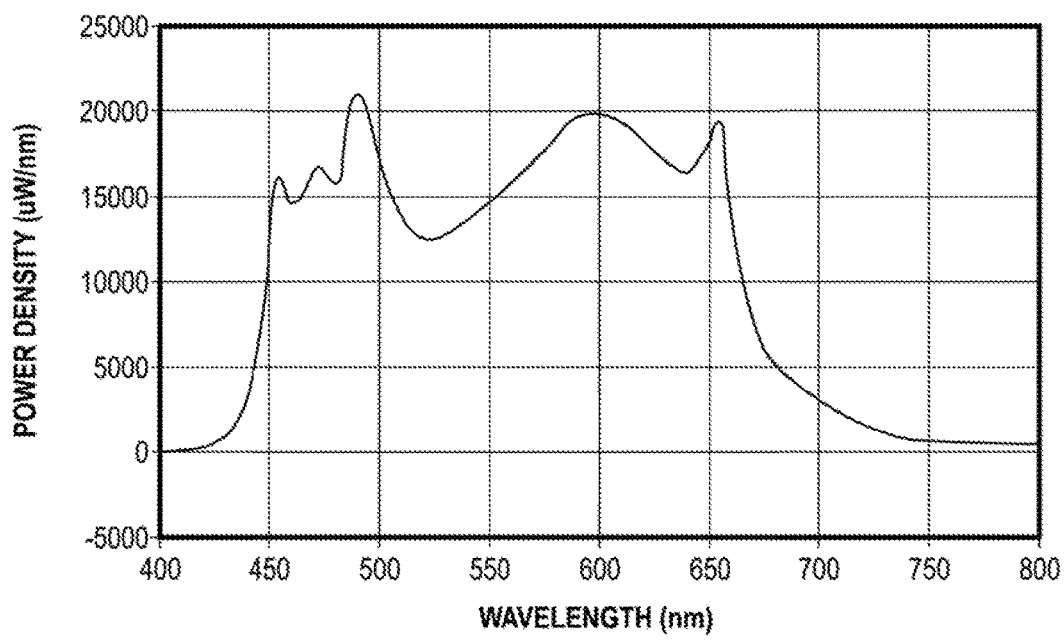

FIG. 5*a* shows a spectral power distribution output of the LED light engine illustrated in FIGS. 4*a-b* according to one embodiment. The output spectrum according to this embodiment is rich in melanopic light (e.g., ipRGC stimulating) as indicated by the spectral peak around 490 nm, Furthermore, the illumination contains much less of the potentially damaging blue light, e.g., light in the 440-460 nm regions, as compared to conventional LED light sources. FIG. 5*b* shows a spectral power distribution output of another LED light engine according to another embodiment. The output spectrum is both rich in melanopic light and contains a reduce amount of so called "blue hazard" light when compared with convention LED sources. Embodiments of the invention include but are not limited to a variety of CCTs, including 2700K, 3000K, 3500 k, 4000 k, 5000 k, etc.

In some embodiments, the initial illumination spectrum generated by the light engine 400 is measured and the electrical current of the tuning LEDs 422, 424 and 426 are adjusted by the nanotuner circuit 430 such that the illumination output spectrum matches a desired or target spectrum. The total output spectrum, comprised of the output spectra of both the LED string 410 and the tuning LEDs 420 is adjusted by selectively varying the light output of the tuning LEDs 422, 424 and 426. The light output of the tuning LEDs is determined by the current flowing through the respective tuning LEDs 422, 424 and 426. By altering the electrical current of each of the tuning LEDs 422, 424 and 426, the relative proportion of current through each of the tuning LEDs and color output of each can be finely controlled and adjusted to achieve a resulting target color point.

As described earlier herein, due to the non-uniformity amongst individual LEDs (due to inherent limitations in manufacturing, binning, etc.) individual LED boards designed and constructed to be identical in spectral output, even though each board may contain the same layout, type and number of LEDs, may each generate slightly different output spectrums. This may be unsatisfactory, for example, to the lighting consumer In one embodiment of the invention, the spectral output of an individual board (or LED fixture) is measured and compared to a known or desired spectral output, and this information is used in conjunction with the nanotuner circuit 430 to adjust the spectral output of tuning LEDs to achieve a consistent target output spectrum. The spectral measurement may be performed with a color sensor, e.g., an off the shelf color sensor. In one embodiment, a TAOS TCS3414CS Digital Color Sensor is employed for the spectral measurement. In some embodiments, the spectral measurement is performed by an external color measurement sensor or otherwise separate or remote calibration or measurement device. In other embodiments, the color measurement sensor is incorporated into the LED light engine itself. In some embodiments where the color measurement is performed by a device external to the light engine, program instructions may delivered, by a device remote from the light engine, to the nanotuner circuit 430 to set the switching and thereby the electrical current through the tuning LEDs 422, 424 and 426 such that the resulting light engine illumination matches a target color point. In some embodiments, the nanotuner circuit is preprogrammed to adjust the electrical current of the tuning LEDs to match one or more specific color points. In some embodiments, the color sensor may be integrated in to the light engine or otherwise part of the lighting fixture, and the color output of light engine monitored continuously by the sensor. The continued monitoring of the color output allows for real time and continuous or intermittent but repeated adjustments by the nanotuner circuit to maintain a specific and consistent color output.

This process of measuring the total spectral output and then adjusting the current flows through the tuning LEDs may be iterative. For example, a closed loop system may be used wherein the total spectral output is continuously (or intermittently) monitored and compared with a target desired output, and the tuning LEDs driven by the nanotuner controller circuit to achieve the target output. In a closed loop system, any drift or other variation in total spectral output may be corrected in real time. In another embodiment, the total spectral output of the LED board may be measured at the factory or manufacturing facility and the current flow through the tuning LEDs determined and set at the factory prior to shipment. In still other embodiments, the appropriate current flow through the tuning LEDs can be programmed at the retail distribution point or may be set by the user by an appropriate interface at other times during the life cycle of the light engine.

As will be evident to those skilled in the art, there are a number of ways to convert raw color sensor data into color tristimulus values and/or CIE color points. Raw color data in the form of RGB information may be converted via a correlation matrix or transform into tristimulus values XYZ, which then may be further transformed to a specific color point (x,y). In some embodiments, a digital color sensor (e.g., TAOS TCS3414CS) senses light from the light engine and measures red(R), green(G), blue(B) irradiance. The RGB irradiance data is used to determine the light engine's CCT and chromaticity coordinates. In some embodiments, the RGB data is mapped to CIE tristimulus values (XYZ) via a correlation matrix (3:3 transform). Chromaticity coordinates (x,y) and correlated color temperature (CCT) are then computed from the tristimulus values (XYZ). A 3:2 transform may be used to obtain color points (x,y) from the tristimulus values (XYZ). CCT can be computed using McCamy's formula for example. A variety of methods and mathematical transformations or algorithms may be used to convert raw RGB sensor data, or other color sensor data, into color coordinates and CCT as will be evident to those skilled in the art, and embodiments of the invention are not limited to any particular method.

A desired or target illumination output may be specified in a number of ways, for example by specifying target tristimulus values (XYZ), chromaticity coordinates (x,y), or correlated color temperature (CCT). In some embodiments, the target illumination output spectrum is specified by a point on the CIE color diagram, i.e., a color point (x,y) or pair of chromaticity coordinates. The microcontroller 432 of the nanotuner circuit 430 may be programmed to generate color points from either raw or processed color sensor data. Alternatively, the microcontroller may receive a determined color point directly from another device. In some embodiments of the invention, the microcontroller 432 of the nanotuner circuit 430 is programmed to adjust the electrical currents of the tuning LEDs 422, 424 and 426 to match one or more target color points that may be pre-programmed into the microcontroller or generated "on the fly" in response to other inputs.

In some embodiments, the individual electrical current, of each of the tuning LEDs 422, 424 and 426, which may correspond to the "on-time" percentages of each of the tuning LEDs, are adjusted such that the resulting illumination from the light engine (i.e., combined illumination from static LED and tuning LEDs) is trimmed towards and reaches the target color coordinates. Adjusting a light engine to produce a specific color point or CCT begins with knowledge of the initial or current color point of the illumination from the light engine (e.g., derived from color sensor data). The electrical currents through each of the tuning LEDs are modified to produce the target color point. Determining the optimal triplet of electrical current for the three tuning LEDs of a light engine, that will trim or adjust a light engine color output to a target color output is performed using coefficient matrix or other conventional mathematical techniques and the algorithm(s) for deriving or determining the appropriate currents are programmed into the nanotuner microcontroller 432 according to some embodiments. In some embodiments, a coefficient matrix will be specific to the color and driving characteristics of each of the tuning LEDs, and will derived based on the specific light engine and tuning LEDs. As will be evident to those skilled in the art, embodiments of the invention are not limited to any specific light engine, tuning LEDs or coefficient matrix, and the method and systems described herein for adjusting a light engine using tuning LED to meet a target color point, including the derivation specific coefficient matrices, are widely applicable and may be accomplished in a variety of ways. Also, embodiments of the invention are not limited to any specific means of adjusting electrical current flow through the tuning LEDs, for instance adjusting the electrical duty cycles of the tuning LEDs, and may be accomplished via a variety of switching and/or current control and delivery approaches.

While some embodiments of the invention utilize four different color LEDs on the light engine, with three of the colors being used in the nanotuner controller, embodiments of the invention include light engines with a total of only three different color LEDs on board. In these embodiments, a total of three different color LEDs are utilized in the light engine and nanotuner controller. In some embodiments, the three color LED types comprise three different color monochromatics LEDs. In some embodiments, the three color LED types comprise two different color monochromatics LEDs and one white LED. In still other embodiments, the three color LED types comprise two different white light LEDs and one monochromatic LED. As will be known to those skilled in the art, mixing of three color LEDs allows for the matching of any color point contained within the triangle formed by the three LED color points.

Figure 6A:
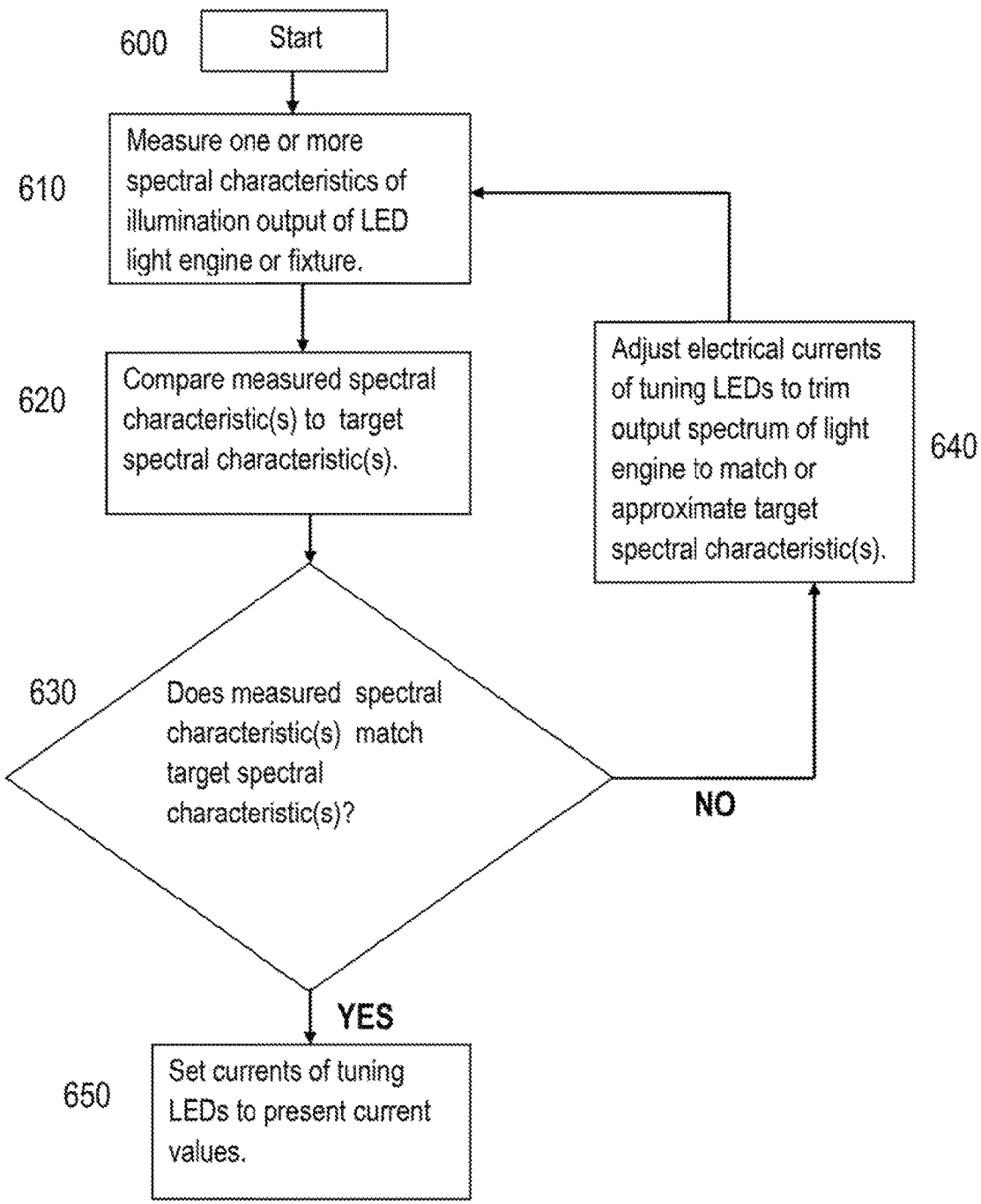
FIGS. 6a-c show process flow algorithms for controlling the light output of LED light engines and tuning them according to some embodiments.
Figure 6B:
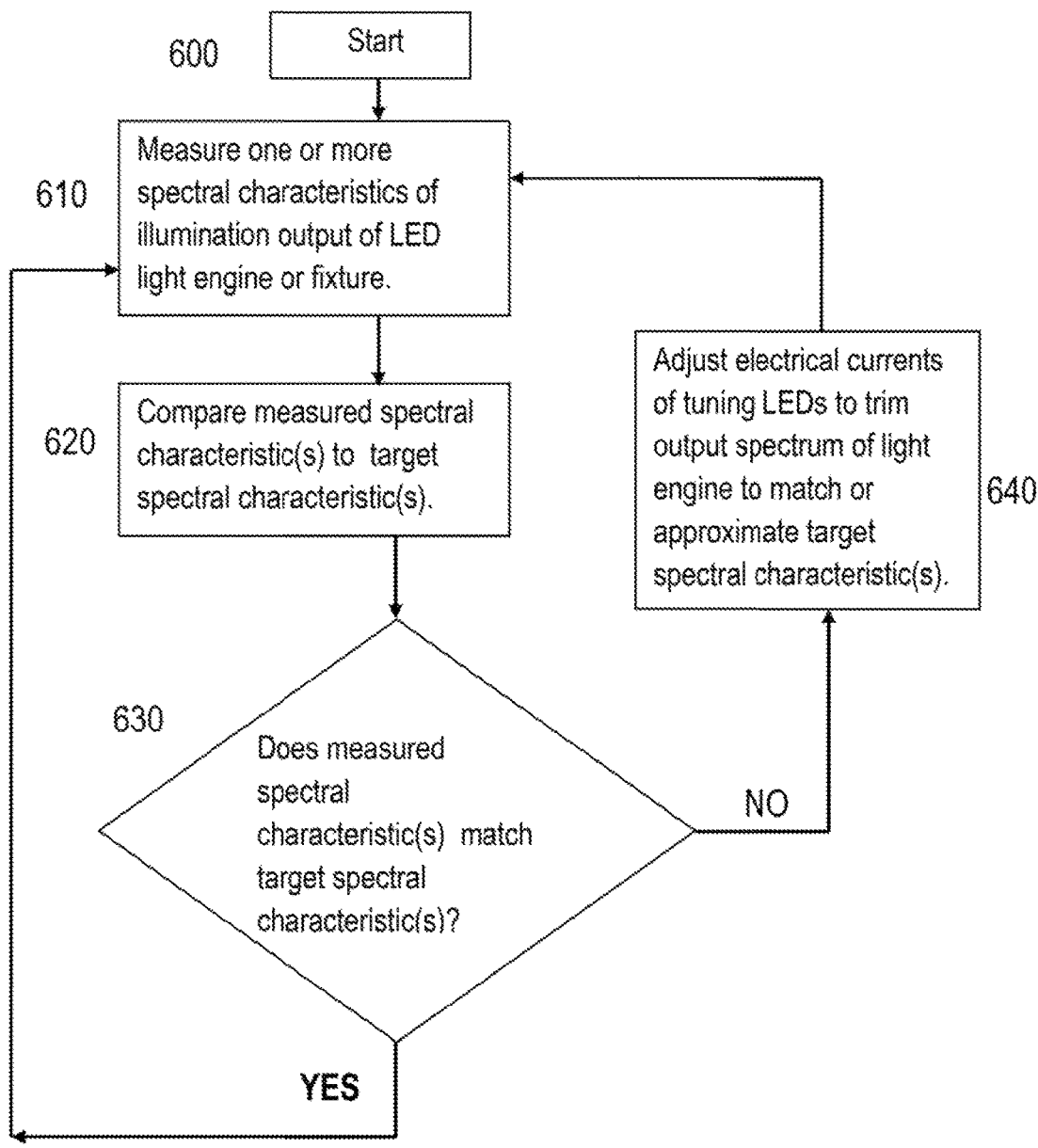
Figure 6C:
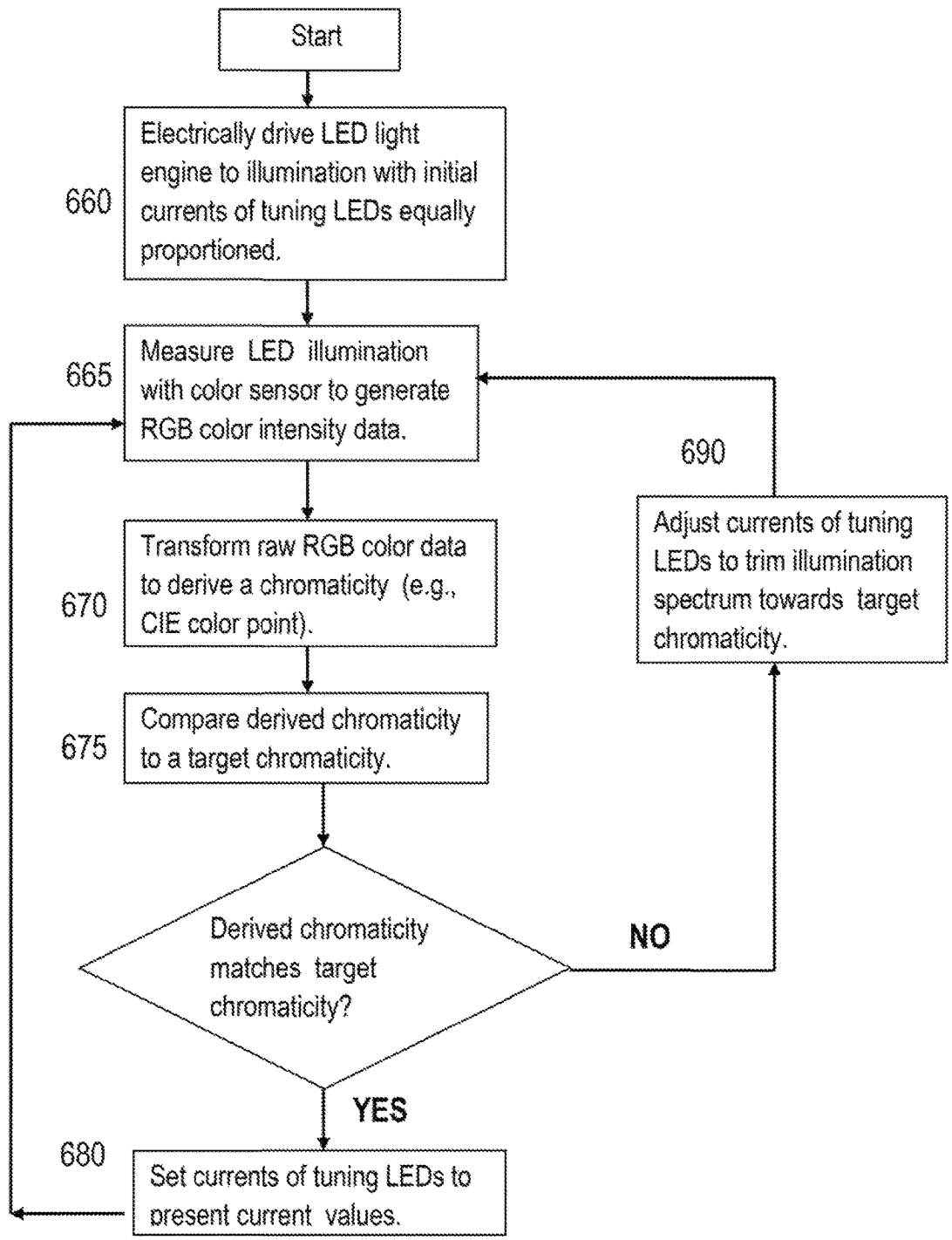

FIGS. 6*a-c* are process low charts illustrating operation of the light engine 400 comprising the nanotuner control circuit 430 and in conjunction with a color light sensor (not shown) according to some embodiments of the invention. According to some embodiments, this functionality of setting the initial electrical currents through the tuning LEDs, comparing of the measured color output of the light engine to a target color output, and adjusting the currents of the tuning LEDs to trim the light engine output such that it matches a target color point is programmed into the nanotuner circuit microcontroller 432. In some embodiments, the microcontroller 432 controls the operation of the color sensor. In some embodiments, a target CCT or color point (x,y) is set and an initial current flow of 33.3% of total light engine current is established for each of the three tuning LEDs 422, 424 and 426. The light engine output is measured via a color sensor and converted to a chromaticity. The converted chromaticity is compared to a target chromaticity, and the relative current flow of the tuning LEDs are adjusted to in order to tune the light engine output to the target chromaticity.

In some embodiments the color or spectral output of the LED light board or fixture is measured. The spectral output sensor (not shown) may be a separate unit from the light engine 400 or nanotuner controller 430 or alternatively the spectral output sensor may be integrated within the LED fixture, or LED board, or nanotuner controller according to the preferred application as described above. In operation the output spectrum of the LED light engine 400 is measured by the spectral output sensor and compared to a known or desired target output spectrum. This comparison may be performed by a separate processor or integrated circuit, but in this embodiment is performed by the nanotuner controller circuit 430. In some embodiments, the nanotuner controller circuit via its microcontroller transforms the raw RGB color data from the color sensor to a chromaticity (e.g., a CIE color point) The deviation in the measured output spectrum from the desired spectrum is eliminated or reduced by adjusting or altering the currents provided to and through each of the tuning LEDs. The nanotuner control circuit 430 performs this functionality. The microprocessor 432 is programmed to control the switching and thereby the electrical currents of the different color tuning LEDs. By calculating, receiving or otherwise retrieving, (e.g., from a look up table), the appropriate electrical operating condition, e.g., current, for each type of tuning LED that would produce a light engine output that matches, approximates or approaches a target color point, the microcontroller controls the switches such that the appropriate electrical operating condition is met, e.g., appropriate current flows through the tuning LEDs thereby trimming the spectral output of the light engine to match the target output (e.g., chromaticity coordinates).

With reference to FIG. 6a, according to some embodiments, the process starts at 600; for example this may be when power is supplied to the LED board 400 and both static LED string 410 and tuning LEDs 420 are illuminated generating an output spectrum. In some embodiments the initial current provided to the tuning LEDs is equally distributed across the three different colors of LED (e.g., each color string of tuning LEDs received one third of the circuit current), but the initial currents to the tuning LEDs may be set at other values as desired through programming the nanotuner controller. One or more spectral characteristics are measured 610 by a spectral sensor. For example, a color sensor is used to measure and output RGB color spectral data. At step 620, the measured spectral characteristics are compared to a target spectrum. In some embodiments, the target spectrum corresponds to a target CIE chromaticity and the measured spectral data is converted to a measured CIE chromaticity for comparison to the target chromaticity. The target chromaticity may be set beforehand by programming the nanotuner controller or alternatively may be provided in real time or on an ongoing basis depending on the application. At step 640, if the measured spectral characteristics do not match the target spectral characteristics, the currents flowing through each of the tuning LEDs 422, 424 and 426 are adjusted such that the resulting output spectrum matches or approaches the target spectral characteristics. This process may be iterative. By adjusting the current flowing through the different color tuning LEDs, and thereby adjusting their respective color brightness, the total output spectrum may be finely tuned in chromaticity and brightness in order to match or closely approximate the desired target spectrum. When the output spectral characteristics sufficiently matches the target spectral characteristics, the current values delivered to each of the tuning LEDs are set and fixed at their current values 650. In some embodiments, the LED board/fixture is initially tuned to the target spectrum and then the electrical currents of the tuning LEDs are fixed and continuous monitoring of the output spectrum is discontinued. Such an embodiment may be appropriate for initially tuning LED board/fixtures to a target spectrum at the factory or other point in the chain of commerce in order to insure uniformity of spectral output.

FIG. 6b shows a process flow of the nanotuner controller according to another embodiment wherein the monitoring of one or more spectral characteristics of the light engine output and adjusting the tuning LEDs to match a target output or color point is continuous (e.g., in real time). In some embodiments, a spectral sensor may be onboard the LED fixture or incorporated into the LED light engine. One or more spectral characteristics are measured 610 by a spectral sensor. The measured spectral characteristics are compared to a target spectrum 620. At step 640, if the measured spectral characteristics do not match the target spectral characteristics, the electrical currents of each of the tuning LEDs are adjusted such that the resulting output spectrum matches or approaches the target spectral characteristics. This process may be iterative and in some embodiments continuous. When the output spectral characteristics sufficiently matches the target spectral characteristics, the electrical currents of the tuning LEDs are maintained at their current values, and the process continues in a loop manner by measuring spectral characteristics of the light engine output 610, comparing the current measurement output to target output 620 and performing any needed adjustment to the output of the tuning LEDs 640 in order to trim the light engine output to the target spectrum.

FIG. 6c shows a process flow diagram according to one embodiment. A light engine comprising tuning LEDs is electrically driven to illumination wherein the initial currents of each tuning LED color is equally proportioned 660 (e.g., each of the tuning LEDs receives ⅓ of the current flowing through the light engine). A color sensor is used to measure the spectral output of the light engine and RGB color data is generated 665. The RGB color data is transformed to derive a CIE color point or chromaticity 670. The derived chromaticity is compared to a target chromaticity 675. If the derived chromaticity matches the target chromaticity, the electrical currents flowing to each of the tuning LEDs are set to or held at their current values 680. If the derived chromaticity does not match the target chromaticity, the currents of the tuning LEDs are adjusted to trim the light engine output spectrum toward the target chromaticity 690. In some embodiments, this process is performed continuously, semi-continuously or intermittently. In some embodiments the process is part of a real-time feedback and adjustment closed loop system.

Figure 7A:
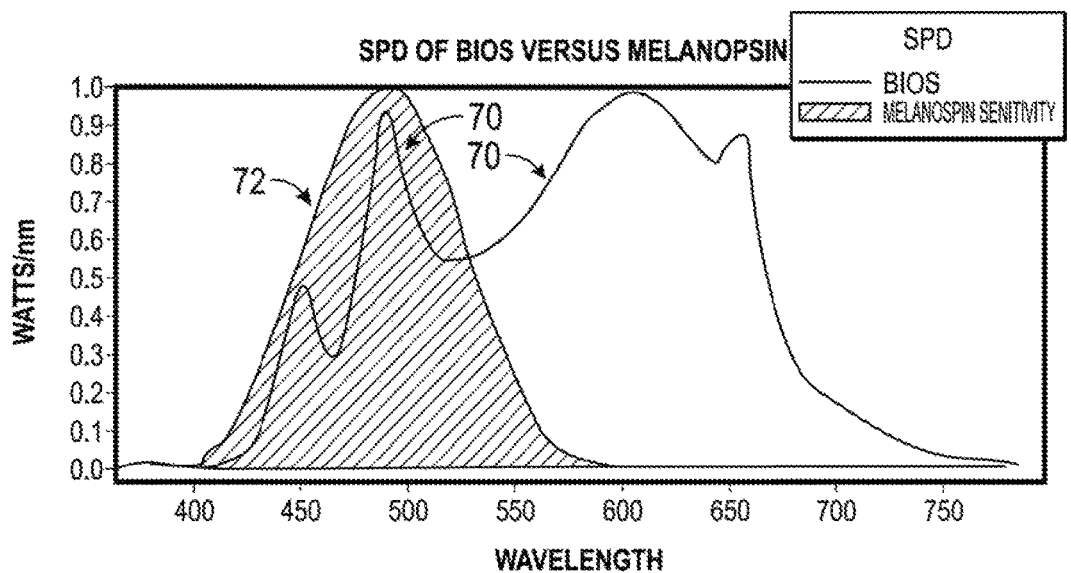
FIGS. 7a-b show a SPDs of illumination provided by some embodiments of the invention overlaid with the melanopsin action spectrum and spectral region of blue light hazard.
Figure 7B:
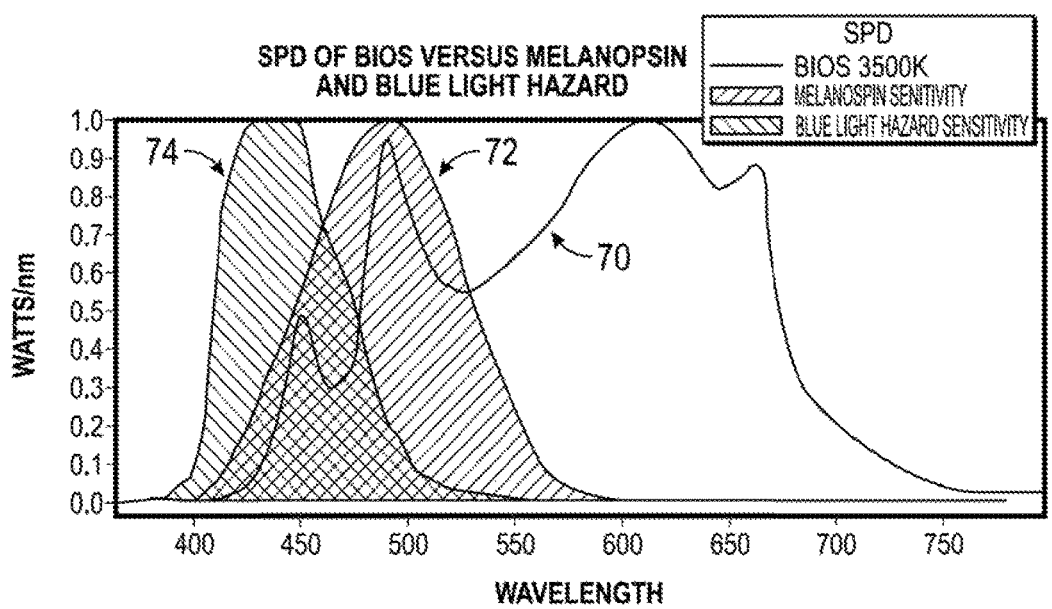

FIG. 7a shows an SPD 70 of illumination provided by an embodiment of the invention overlaid with the melanopsin action spectrum 72. The spectral outputs produced by embodiments of the invention are rich in biologically important light while providing light of high efficacy, high CRI and esthetic appeal. FIG. 7b shows an SPD 70 of illumination provided by an embodiment of the invention overlaid with the melanopsin action spectrum 72 and blue light hazard spectral region 74. As compared to convention LED sources, embodiments of the invention provide high efficiency and attractive white light with important biological spectral components and with reduced amount of light in the blue light hazard spectral region.

Another approach, and according to some embodiments of the invention, in order to provide adequate melanopic flux while reducing potential blue light hazard, a blue pump LED at or near 450 nm (e.g., outside the blue hazard region or with less blue hazard impact) and one or more broadband phosphors are used to produce highly efficacious white light. The use of a 450 nm LED pump avoids using higher frequency pumps in the blue light hazard region. In some embodiments, use of a 450 nm LED pump may produce white light that is over-converted, that is, the resultant output spectrum is not "blue" enough because the majority of the blue light from the pump has been down-converted for the desired resultant color temperature. In some embodiments, in order to address this issue, an additional monochromatic LED with peak emission at or near 490 nm is added to the light engine. In still other embodiments, an additional red LED or other red emitter (e.g., phosphor) is added to provide a resultant output spectrum that resides on or near the black body curve or locus.

Other embodiments include narrow band down converters, such as quantum dots or narrow emission phosphors in the 490 nm region. Likewise, narrow emission spectrum in the red region can come from specialty phosphors or quantum dots. In some embodiments, the resultant output spectrum expands over the entire region from 600-100 nm. In some embodiments, this spectrum is achieved using efficient LEDs near 660 nm in conjunction with phosphors, peaking between 760 nm to 860 nm.

As discussed elsewhere herein, challenges to producing a uniform white light of consistent color are present when the resultant white light is high in relative melanopic flux (i.e., strong or peak emissions in the 490 nm region). These challenges are due, inter alia, to fact that the sensitivity of the individual retinal cones are highly variable in this spectral region (e.g., the action spectrum slope of different cone types runs in opposite direction and leads to a heightened discrimination by the visual system of slight deviations in output spectrum). Thus, the non-uniformity of LED packages due to manufacturing and binning limitations may result in identically designed LED boards and engines that have noticeable differences in output spectra.

In order to compensate for aberrations in color output and correct and insure uniformity, and according to some embodiments, one or more specific phosphors and/or quantum dots are directly applied to white light packages to alter their (x,y) color coordinate position in order to adjust them to one or more specific color points and/or insure uniformity of color output. In some embodiments, the type and amount of phosphor or lumiphoric material to be applied is dependent on the difference between the actual color point of the emitter and a target color point.

For example, if measured peak emission of an emitter shows a peak emission of 491 nm whereas the emitter is targeted to emit at 490 nm, a noticeable shift of perceived color in the y direction could result. According to some embodiments, this aberration is rectified by applying a small amount of pinkish phosphor with (x,y) color coordinate directly below the black body such that the new light output is appropriately trimmed for color uniformity and for example brought onto the black body locus. Other examples of applying one or more specific phosphors and/or quantum dots or other lumiphoric materials to finely adjust the color temperature of individual LED packages and/or LED light engines or boards will be evident to those skilled in the art. Means and mechanisms for applying phosphors and/or quantum dots or other lumiphors include but are not limited to the application of liquids with lumiphoric materials dispersed therein, screen or ink-jet printing, colloidal or sol-gel applications, deposition via mixing of lumiphors with silicone or epoxy, direct injection, lithography, lamination, etc. It should be noted, that a variety of means and methods of applying phosphors and other lumiphoric materials to LED dies and packages are known by those skilled in the art, and embodiments of the invention are not limited to any particular method.

In some embodiments, the process of depositing phosphors and/or quantum dots is performed after LED board or engine fabrication and provides a means for bringing each light engine or board into spectral output color uniformity. In some embodiments, the illumination output spectrum of a light engine is measured and compared to a target output spectrum. If there is a difference that meets a certain threshold, phosphor (and/or quantum dots) are added to one or more of the LED packages to trim the resultant output spectrum of the light engine to match the target spectrum. In some embodiments, phosphor is removed from the package in order to trim the color point. This process may be iterative.

Figure 8A:
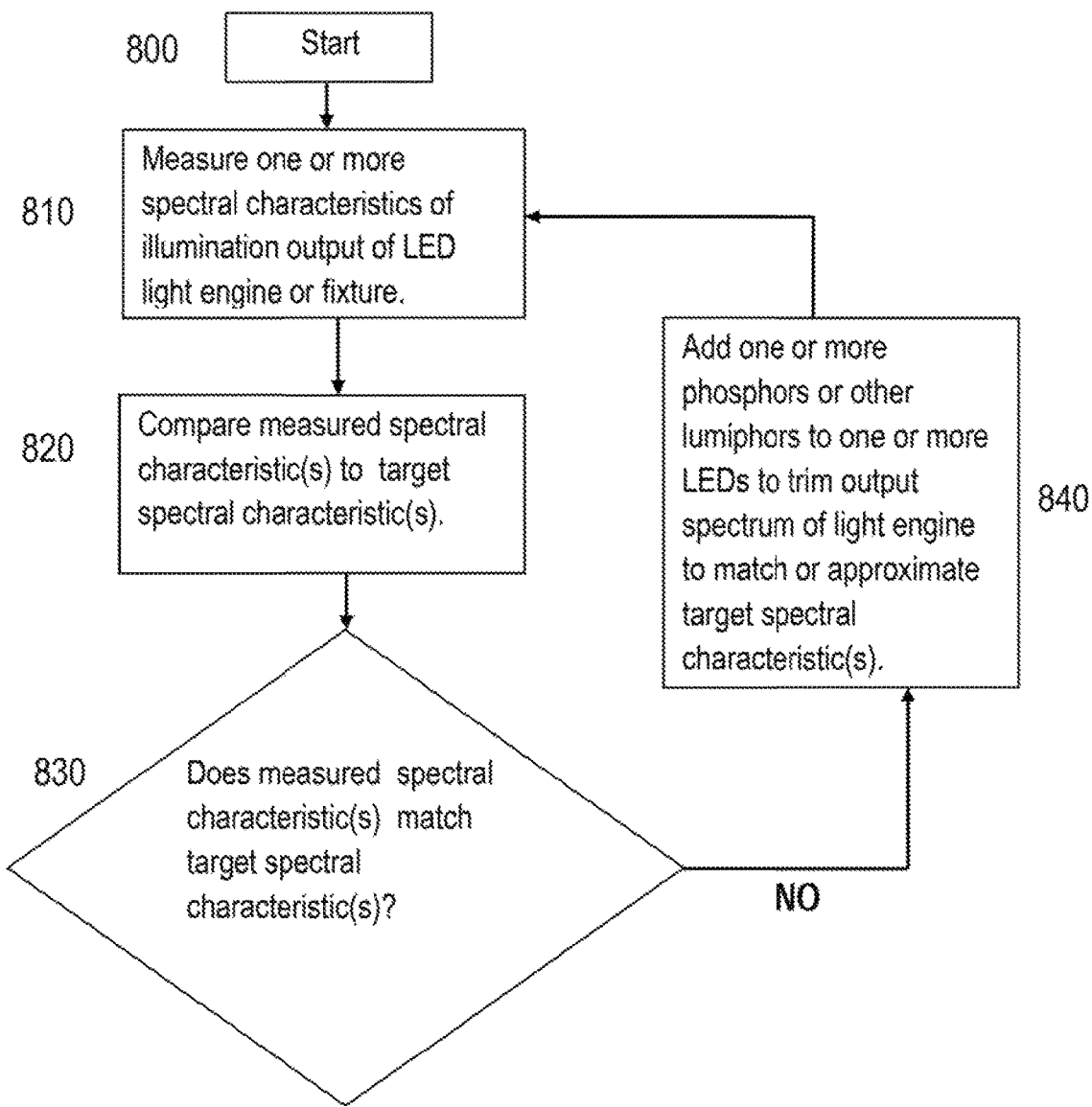
FIGS. 8a-b show process flow algorithms for controlling the light output of LED light engines and tuning them according to some embodiments.
Figure 8B:
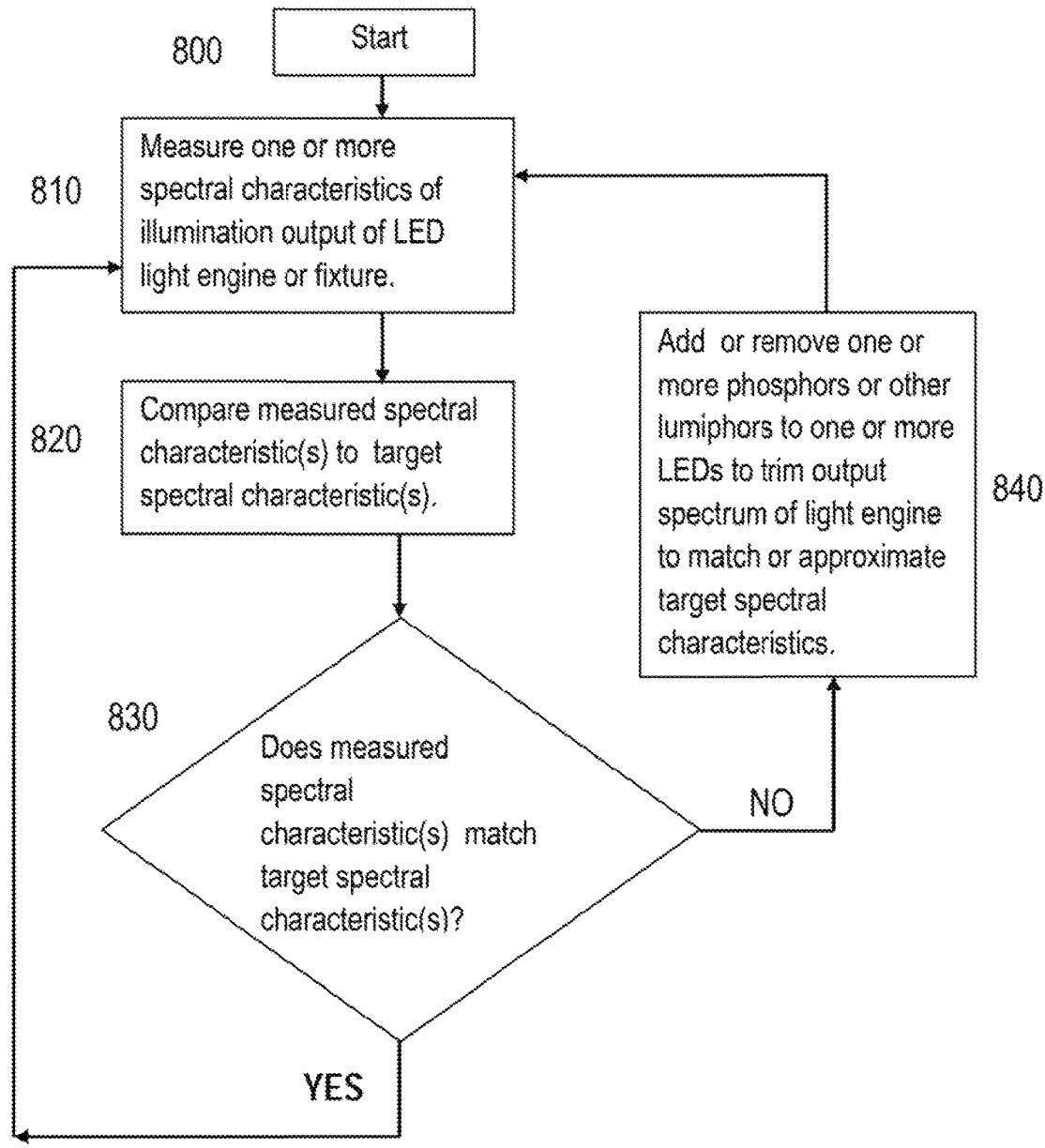

Examples of processes according to some embodiments are shown in FIGS. 8a-b. With reference to FIG. 8a, according to some embodiments, the process starts at 800; for example this may be when power is supplied to the LED board. One or more spectral characteristics are measured 810 by a spectral sensor. At step 820, the measured spectral characteristics are compared to a target spectrum. In some embodiments, the target spectrum corresponds to a target CIE chromaticity and the measured spectral data is converted to a measured CIE chromaticity for comparison with target chromaticity. The target chromaticity may be set beforehand by programming the nanotuner controller or alternatively may be provided in real time or on an ongoing basis depending on the application. At step 840, if the measured spectral characteristics do not match the target spectral characteristics, one or more phosphors or other lumiphors are added to one or more of the LEDs thereby trimming the output spectrum of light engine to match or approximate target spectral characteristics. In some embodiments, application of the phosphor occurs while the LED is powered and illuminating. In other embodiments, the LEDs are powered off for the application of the phosphor.

FIG. 8b shows a process flow of the nanotuner controller according to another embodiment wherein the monitoring of one or more spectral characteristics of the light engine output and applying or removing lumiphors to match a target output or color point is iterative. In some embodiments, a spectral sensor may be onboard the LED fixture or incorporated into the LED light engine. One or more spectral characteristics are measured 810 by a spectral sensor. The measured spectral characteristics are compared to a target spectrum 820. At step 840, if the measured spectral characteristics do not match the target spectral characteristics, lumiphor(s) are added and/or removed to trim output spectrum of light engine to match or approximate target spectral characteristics.

In other embodiments, the applying of the phosphor or quantum dots occurs during the package level manufacturing process. For example, LED manufacturers could add small amount of material during the binning process to bring the LED packages into color uniformity. In some embodiments, the process of fine tuning the light output color involves removing small portions of phosphor or other lumiphors.

It will be understood, and evident to one skilled in the art, that although these examples shows specific LED light sources (e.g., with specific color outputs and intensities) and specific numbers and ratios of LEDs, the inventive concepts disclosed herein are not limited to any specific set of LEDs, types or ratios of same. A variety of different LEDs, phosphor pumped "white" LED and/or monochromatic LED may be arranged and configured and driven by appropriate current to produce a desired or target output spectrum.

Additional Embodiments

There are biological pathways in the human body that are light driven or otherwise influenced by light exposure. Circadian regulation has a dedicated photoreceptor in the eye, most sensitive to a blue/green light, light similar to that found in a blue sky. A photoreceptor has also been found in mitochondria. When cellular mitochondrial photoreceptors are irradiated by certain types (e.g., wavelengths and wavelength ranges) of red light, increased mitochondrial activity including production of ATP results leading to higher densities of ATP in the cells. The increased synthesis of ATP in isolated mitochondria and intact cells of various types under irradiation with monochromatic light of different wavelengths is well documented. Other intracellular and extracellular manifestations may also be involved.

As a neurotransmitter, ATP is directly involved in brain function, sensory reception, and the neuron system control of muscles and organs. When released by non-neuronal cells, it often triggers protective responses, such as bone building and cell proliferation. ATP is now believed to play a role as the signaling molecule, and a long series of discoveries has demonstrated that ATP is not only an energy currency inside cells, but it is also a critical signaling molecule that allows cells and tissues throughout the body to communicate with one another. Some hypotheses hold that the switch from wake to sleep appears to correlate with the accumulation of the ATP breakdown product adenosine during wakefulness. ATP and its derivatives appear to play roles in the circadian cycle including the sleep/wake cycles including sleep pressure buildup and may involve intercellular signaling between non-neuronal and neuronal cells thereby influencing the sleep-wake cycle including subjective feelings of sleepiness or alertness.

Skin has an "optical and near IR window" receptive to light between 630 nm-900 nm. This window allows for deep penetration into the cells, where mitochondria is present. Not wishing to be bound by any theory, it is believed that exposure, e.g., of the skin, to deep red light results in increased mitochondrial activity of dermal, sub-dermal and other light receiving cells, resulting in, inter alia, increased ATP production in the respective cells. This increased mitochondrial activity via the exposure of the skin to deep red (and specific wavelength regions of infrared as well) light may play a role in influencing the circadian rhythm or otherwise affect sleep pressure or alertness.

Light-based illumination has been found to be more effective in a pulsed form for skin-based applications. Additionally, the recently discovered photoreceptors involved in circadian regulation have been shown to have a much slower response time than visual photoreceptors, such as rods and cones. Thus, pulsing light intermittently below a certain frequency, while adequately stimulating the visual receptors, rods and cones, will have a smaller stimulating effect on the opsins and other circadian related photoreceptors. The melanopic response, and impact on circadian rhythm entrainment, may therefore be less with pulsed light than compared to a continuous stream of light of equal visual stimulus. The pulsing of light to attenuate or mitigate any melanopic response may be achieved at pulse rates that do not alter visual perception, e.g., the pulsing occurs at a frequency that is greater than the visual criteria for visible flicker which occurs at about 50 Hz.

The effect on the circadian cycle as well as on sleep pressure and alerting response of light exposure at night is one that is highly influenced by daytime biological stimulus including light stimulus. For example, a construction worker who spends most of his days outdoors will experience a smaller impact from light at night compared to someone who spends more of the day in a computer lab with low light levels. This response is dynamic over the course of a day. First morning light helps stimulate cortisol awakening response. Likewise, adaptation for the circadian system is heavily influenced by the light exposure most recently preceding night time or darkness. For example, a high biological light exposure in the late afternoon is also beneficial to circadian regulation and rhythm.

Additionally, circadian related photoreceptors are in macular and peripheral vision nearest to the fovea. Thus a light source that produces high biological light in this region is ideal. Melanopsin related photoreceptors are most sensitive in the lower hemisphere of the retina. Selective stimulation of these photoreceptors is possible by directing illumination, and specifically melanopic light, towards or away from the region of the retinal where melanopic photoreceptors are most concentrated or most sensitive or responsive.

Embodiments of the invention include methods, systems and luminaires that dynamically generate high efficacy white light that comprises enhanced spectral components that vary at different times of the day to facilitate circadian regulation or entrainment. Embodiments of the invention include dynamic illumination methods and systems for providing relatively high melanopic flux during the day and relatively low melanopic flux at night. Other embodiments of the invention include lighting systems which provide for illumination systems that comprise enriched or depleted melanopic light from above such that exposure of melanopic light to photoreceptors in the lower hemisphere of the retina may be amplified or attenuated based on time of day in order to facilitate circadian rhythm regulation.

In some embodiments, a daytime spectrum is generated that has an enhanced circadian spectrum, i.e., melanopic light around 490 nm (or 480 nm-500 nm). In some embodiments illumination includes enhanced spectral components that are relevant to the skin optical window and sub dermal cellular stimulation (e.g., deep-red around 660 nm and/or infrared). Illumination spectrums produced by embodiments of the invention can increase biological stimulus at times where biological sensitivities are greatest. In some embodiments, illumination provided during nighttime will have relatively lower amounts of 480 nm light (i.e., melanopic light), than for example the illumination provided during the daytime. In some embodiments, illumination is produced by, inter alia, pulsing light of particular wavelength regions. For example, light that may have an adverse impact on circadian response or rhythm at a particular time of day, e.g., melanopic light at nighttime, may be pulsed during this time in order that the opsin responsive photoreceptors are less stimulated thereby reducing the impact of this light on the circadian system. The slower response of the circadian relevant photoreceptors and decreased cumulative photonic stimulation incident on the photoreceptor due to the pulsing of the light mitigates or attenuates any adverse circadian impact. Pulsing of the light may be of sufficient frequency such that it has no visual impact (e.g., light is pulsed above the flicker rate). Embodiments of the invention includes systems and luminaires that can alter the illumination spectrum at different times of the day, for examples dynamic systems that can dynamically change the illumination spectrum over the course of a day. In some embodiments relatively higher amounts of deep-red or infrared light (or light in that optical region) are provided during specific times of day to facilitate biological responses including circadian regulation or changes to alertness.

In some embodiments, blue light in the 420 nm region is employed in a lighting system to provide illumination that results in an acute alerting affect. In some embodiments, this illumination is depleted in melanopic light (e.g., in 490 nm or 460-500 nm) and thereby produces an alerting effect while providing no or reduced impact on the circadian rhythm. The lighting system according to these embodiments produces white light illumination with both high CRI and aesthetic appeal.

Other embodiments of the invention include methods, luminaires and systems for providing biologically relevant light (e.g., melanopic light) from indirect illuminating sources. Embodiments include using white light and/or monochromatic sources, and examples include cove lighting and indirect ceiling and floor lighting. Some embodiments include illumination systems that provide light, that may effect a biological stimulus (e.g., melanopic light), from below such that the light impacts the upper hemisphere of the retina where the opsin photoreceptors are less sensitive thereby reducing the potential biological stimulus. Embodiments include lighting, indirect light, from above which is depleted of melanopic light but of high CRI thus providing aesthetic white light but without or with reduced biologically stimulating light.

While the invention has been described with reference to exemplary embodiments, it will be understood by those skilled in the art that various changes may be made and equivalents may be substituted for elements thereof without departing from the scope of the invention. It should be understood that the diagrams herein illustrates some of the system components and connections between them and does not reflect specific structural relationships between components, and is not intended to illustrate every element of the overall system, but to provide illustration of the embodiment of the invention to those skilled in the art. Moreover, the illustration of a specific number of elements, such as LED drivers power supplies or LED fixtures is in no way limiting and the inventive concepts shown may be applied to a single LED driver or as many as desired as will be evident to one skilled in the art.

In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include many variants and embodiments. Also, in the drawings and the description, there have been disclosed exemplary embodiments of the invention and, although specific terms may be employed, they are unless otherwise stated used in a generic and descriptive sense only and not for purposes of limitation, the scope of the invention therefore not being so limited. Moreover, the use of the terms first, second, etc, do not denote any order or importance, but rather the terms first, second, etc. are used to distinguish one element from another. Furthermore, the use of the terms a, an, etc, do not denote a limitation of quantity, but rather denote the presence of at least one of the referenced item.

What is claimed is:

1. A method for generating illumination from a light source and tuning the spectral output of the light source comprising the steps of:
    providing a light engine comprising at least: one LED of a first color, one LED of a second color, one LED of a third color and one LED of a fourth color and wherein the light engine also comprises electrical circuitry for selectively driving LEDs constituent of said light engine;
    electrically driving said light engine to produce a first illumination;
    providing a target color point illumination for the light engine;
    measuring the color of said first illumination and comparing it to said target color point; and
    adjusting the illumination output of at least one of the first color LED, the second color LED, the third color LED and the fourth color LED by selectively adding a phosphor or other lumiphoric material to the LED such that the color of the resulting illumination output of the light engine matches said target color point illumination.

2. The method of claim 1 wherein the lumiphoric material comprises one or more quantum dots.

3. The method of claim 1 wherein the first color LED comprises a blue pump LED emitting a peak wavelength at or about 450 nm and one or more phosphors.

4. The method of claim 1 wherein at least one of the color LEDs is a white light producing LED and at least two of the other color LEDs are monochromatic LEDs each producing a different color.

5. The method of claim 4 wherein the LED of the second color approximates the color cyan or about 490 nm, and the LED of the third color emits at a peak wavelength greater than 600 nm.

6. The method of claim 1 wherein said measuring the color output of said first illumination is performed using a measuring device separate from and not integrated with said light engine.

7. The method of claim 1 further comprising the step of adjusting the illumination output of one or more of the first color LED, the second color LED, the third color LED and the fourth color LED by altering the electrical current flowing through the respective LED.

8. The method of claim 7 wherein the altering of the electrical current flowing through an LED is accomplished by programming an electrical switching circuit of the light engine wherein the switching circuit controls the current flows to each of the respective LEDs.

9. The method of claim 1 wherein said target color illumination corresponds to a point on the C.I.E. chromaticity diagram on or proximal to the black body curve.

10. A method for controlling the output spectrum of a light engine comprising the steps of:
    measuring spectral characteristics of an illumination output of a light engine that is electrically driven to illumination wherein the light engine comprises a first color LED, a second color LED, and a third color LED and wherein the light engine also comprises electrical circuitry for selectively driving LEDs constituent of said light engine and converting said measured spectral characteristics to a measured chromaticity;
    comparing said measured chromaticity with a target chromaticity; and
    selectively adding a phosphor or other lumiphoric material to at least one of the first color LED, the second color LED and the third color LED whereby the resultant respective illumination from one or more of the LEDs to which the phosphor or lumiphoric material has been added is modified such that the chromaticity of the illumination output of the light engine matches or approximates the target chromaticity.

11. The method of claim 10 further comprising the step of removing phosphor or other lumiphoric material from one or more of the LEDs in order to modify the illumination output of the light engine.

12. The method of claim 10 wherein the LED of the first color is a white light producing LED and the LED of the second color is a monochromatic LED and the LED of the third color is a monochromatic LED.

13. The method of claim 12 wherein said white light producing LED of the first color comprises a pump LED emitting light of peak wavelength of about 450 nm.

14. The method of claim 12 wherein the second color LED is a monochromatic LED emitting at a peak wavelength of about 490 nm and the third color LED is a monochromatic LED emitting at a peak wavelength greater than about 600 nm.

15. The method of claim 10 further comprising the step of the adjusting the illumination output of at least one of the first color LED, the second color LED and the third color LED by altering the electrical current flowing through one or more of the respective LEDs.

16. The method of claim 15 wherein the altering of the electrical current flowing through the respective color LEDs is accomplished via a switching circuit comprising a microcontroller that is integral with said light engine.

17. A method for generating illumination that produces white light with adequate melanopic flux, reduced blue light hazard flux and color uniformity and which is capable of being tuned to generate a specific spectral illumination output comprising:
- providing a light engine comprising electrical circuitry for selectively driving light engine LEDs, a first color LED, a second color LED, and a third color LED each configured to receive an input electrical current and generate respective illuminations of the first color, the second color and a third color;
- electrically driving said light engine to produce a first illumination;
- providing a target color point illumination for the light engine;
- measuring the color of said first illumination and comparing it to said target color point; and
- adjusting the illumination output of at least one of the first color LED, the second color LED and the third color LED by selectively adding a phosphor or other lumiphoric material to the LED such that the color of the resulting illumination output of the light engine matches said target color point illumination.

18. The method of claim 17 wherein the first color LED is a polychromatic emitting LED comprising a pump with peak emission between 445 nm and 465 nm.

19. The method of claim 17 wherein the second color LED is a monochromatic LED emitting at a peak emission of between 460 nm and 500 nm.

20. The method of claim 17 wherein one or more quantum dots or lumiphoric nano-particles are added to one or more of the LEDs to alter the color of their respective illuminations.

* * * * *